United States Patent
Min et al.

(10) Patent No.: US 10,758,730 B2
(45) Date of Patent: Sep. 1, 2020

(54) METHOD AND DEVICE FOR CONTROLLING LEFT UNIVENTRICULAR PACING THERAPY

(71) Applicant: PACESETTER, INC., Sylmar, CA (US)

(72) Inventors: Xiaoyi Min, Simi Valley, CA (US); Kyungmoo Ryu, Palmdale, CA (US); Stuart Rosenberg, Castaic, CA (US); David Muller, Sicklerville, NJ (US)

(73) Assignee: Pacesetter, Inc., Sylmar, CA (US)

( * ) Notice: Subject to any disclaimer, the term of this patent is extended or adjusted under 35 U.S.C. 154(b) by 248 days.

(21) Appl. No.: 15/672,178

(22) Filed: Aug. 8, 2017

(65) Prior Publication Data
US 2019/0046802 A1 Feb. 14, 2019

(51) Int. Cl.
*A61N 1/368* (2006.01)
*A61N 1/365* (2006.01)
*A61N 1/05* (2006.01)

(52) U.S. Cl.
CPC ........... *A61N 1/3682* (2013.01); *A61N 1/056* (2013.01); *A61N 1/36585* (2013.01); *A61N 1/36842* (2017.08); *A61N 1/36843* (2017.08)

(58) Field of Classification Search
None
See application file for complete search history.

(56) References Cited

U.S. PATENT DOCUMENTS

| | | |
|---|---|---|
| 7,778,706 B1 | 8/2010 | Min |
| 8,442,634 B2 | 5/2013 | Min et al. |
| 8,565,880 B2 | 10/2013 | Dong et al. |
| 2004/0147966 A1 | 7/2004 | Ding |

(Continued)

FOREIGN PATENT DOCUMENTS

WO 2017074999 A1 5/2017

OTHER PUBLICATIONS

European Search Report dated Oct. 8, 2018; Application No. 18186494.3.

*Primary Examiner* — Erica S Lee
(74) *Attorney, Agent, or Firm* — The Small Patent Law Group LLC; Dean D. Small

(57) ABSTRACT

Methods, devices and program products are provided for controlling a left univentricular (LUV) pacing therapy using an implantable medical device. Electrodes are configured to be located proximate to an atrial (A) site, left ventricular (LV) site and right ventricular (RV) site of the heart. A conduction different Δ is determined based on i) an atrial-ventricular conduction delay ($AR_{RV}$) between the A site and the RV site, and ii) an atrial-ventricular conduction delay ($AR_{LV}$) between the A site and the LV site. A correction term ε is based on intrinsic inter-ventricular conduction delay (IVCD) between the LV and RV. An LV atrial-ventricular pacing ($AV_{LV}$) delay is set based on the conduction difference Δ, a pacing latency PL and the correction term ε and manages the LUV pacing therapy based on the $AV_{LV}$ delay, wherein the LUV pacing therapy lacks pacing in the RV.

20 Claims, 12 Drawing Sheets

(56) References Cited

U.S. PATENT DOCUMENTS

| | | | |
|---|---|---|---|
| 2004/0193223 A1* | 9/2004 | Kramer | A61N 1/3627 607/9 |
| 2005/0209649 A1* | 9/2005 | Ferek-Petric | A61N 1/36514 607/17 |
| 2006/0047320 A1 | 3/2006 | Ding et al. | |
| 2006/0235481 A1* | 10/2006 | Fogoros | A61N 1/3627 607/24 |
| 2008/0269826 A1 | 10/2008 | Lian | |
| 2010/0069987 A1 | 3/2010 | Min et al. | |
| 2010/0145405 A1 | 6/2010 | Min | |
| 2010/0222834 A1 | 9/2010 | Sweeney | |
| 2011/0098772 A1* | 4/2011 | Min | A61N 1/36185 607/28 |
| 2011/0137369 A1* | 6/2011 | Ryu | A61N 1/368 607/27 |
| 2012/0165892 A1* | 6/2012 | Min | A61N 1/36585 607/25 |

* cited by examiner

INTERVENTRICULAR CONDUCTION

METHOD AND DEVICE FOR CONTROLLING LEFT UNIVENTRICULAR PACING THERAPY

BACKGROUND

Embodiments of the present disclosure generally relate to methods and devices for controlling a left univentricular pacing therapy.

Clinical studies related to cardiac pacing have shown that an optimal atrio-ventricular pacing delay (e.g., AV delay or PV delay) and/or an optimal interventricular pacing delay (e.g., VV delay) can improve cardiac performance. However, such optimal delays depend on a variety of factors that may vary over time. Thus, what is "optimal" may vary over time. An optimization of AV/PV pacing delay and/or VV pacing delay may occur at implantation and sometimes, a re-optimization may occur during a follow-up consultation. While such optimizations are beneficial, the benefits may not be long lasting due to changes in various factors related to device and/or cardiac function. Various systems and methods are provided for allowing a pacemaker or IMD to determine and/or adjust AV/PV/VV pacing delays so as to help maintain the pacing delays at optimal values. In particular, techniques were set forth for exploiting various interventricular conduction delays to determine optimal AV/PV/VV pacing delays. Techniques were also set forth for exploiting the VV delays to determine which ventricles should be paced—the left ventricle (LV), the right ventricle (RV), both ventricles, or neither.

Other techniques have been set forth for determining AV/PV delays based on inter-atrial conduction delays and interventricular conduction delays. In particular, see U.S. Pat. No. 7,248,925, to Bruhns et al., entitled "System and Method for Determining Optimal Atrioventricular Delay based on Intrinsic Conduction Delays," which is fully incorporated by reference herein.

Most conventional pacing algorithms call for pacing in the right ventricle (RV) alone or in combination with left ventricular (LV) pacing. However, certain patients may exhibit circumstances where RV pacing may not be necessary. For example, patients may exhibit atria-ventricular conduction delays in certain ranges where pacing in the left ventricle is effective without a need for RV pacing.

SUMMARY

In accordance with embodiments herein a method is provided for controlling a left univentricular (LUV) pacing therapy using an implantable medical device (IMD). The method provides electrodes configured to be located proximate to an atrial (A) site, left ventricular (LV) site and right ventricular (RV) site of the heart. The method utilizes one or more processors to perform determining a conduction different $\Delta$ based on i) an atrial-ventricular conduction delay ($AR_{RV}$) between the A site and the RV site, and ii) an atrial-ventricular conduction delay ($AR_{LV}$) between the A site and the LV site. The method determines a correction term $\epsilon$ based on intrinsic inter-ventricular conduction delay (IVCD) between the LV and RV. The method sets an LV atrial-ventricular pacing ($AV_{LV}$) delay based on the conduction difference $\Delta$, a pacing latency PL and the correction term $\epsilon$ and manages the LUV pacing therapy based on the $AV_{LV}$ delay, wherein the LUV pacing therapy lacks pacing in the RV.

Optionally, the $AV_{LV}$ delay may be based on an interventricular pacing (VV) delay that may be set based on the following: VV=FCTR ($\Delta*W_1+\epsilon*W_2+PL*W_3$). The FCTR may be any desired non-zero number, and $W_1$-$W_3$ represent weighting factors. The method may determine the atrial-ventricular conduction delay ($AR_{RV}$) between the A site and the RV site and and set the $AV_{LV}$ delay based on a difference between the $AR_{RV}$ and the VV delay. The method may measure the pacing latency PL by measuring a latency interval between a paced event, delivered at the LV site, and an evoked response, sensed at the LV site. The method may compare the pacing latency with a threshold and adjusting the VV delay based on the comparison.

Optionally, the adjusting may include setting the interventricular pacing delay VV delay based on the conduction difference $\Delta$ and the correction term $\epsilon$, and not the pacing latency PL when a difference between the IACD and $AR_{LV}$ exceeds a threshold. The method may confirm the LUV pacing therapy using at least one of QRS related feedback, mechanical di-synchrony related feedback or stroke volume surrogate related feedback. The method may analyze a paced QRS width in connection with multiple $AV_{LV}$ delays, and selecting an $AV_{LV}$ delay corresponding to the paced QRS width having a criteria of interest. The, method may analyze a contractility time delay in connection with multiple $AV_{LV}$ delays, and selecting an $AV_{LV}$ delay corresponding to the contractility time delay having a criteria of interest. The method may further comprise analyzing a stroke volume impedance in connection with multiple $AV_{LV}$ delays, and selecting an $AV_{LV}$ delay corresponding to the stroke volume impedance having a criteria of interest.

In accordance with embodiments herein, a system is provided for controlling a left univentricular (LUV) pacing therapy using an implantable medical device (IMD). The system comprises electrodes configured to be located proximate to an atrial (A) site, left ventricular (LV) site and right ventricular (RV) site of the heart. The memory stores program instructions. One or more processors are configured to implement the program instructions to perform determining a conduction different $\Delta$ based on a difference between i) an atrial-ventricular conduction delay ($AR_{LV}$) between the A site and the LV site, and ii) an atrial-ventricular conduction delay ($AR_{LV}$) between the A site and the RV site ($\Delta=AVCD_{LV}-AVCD_{RV}$), determining a correction term $\epsilon$ based on intrinsic inter-ventricular conduction delay (IVCD) between the LV and RV ($\epsilon=IVCD_{LV}-IVCD_{RV}$), setting an LV atrial-ventricular pacing ($AV_{LV}$) delay based on the conduction difference $\Delta$, a pacing latency PL and the correction term $\epsilon$ and managing the LUV pacing therapy based on the $AV_{LV}$ delay, wherein the LUV pacing therapy lacks pacing in the RV.

Optionally, the memory may be configured to store $AV_{LV}$ delay that may be based on an interventricular pacing (VV) delay that is set based on the following: VV=FCTR ($\Delta*W_1+\epsilon*W_2+PL*W_3$). The FCTR may be any desired non-zero number, and $W_1$-$W_3$ represent weighting factors. The one or more processors may be further configured to determine the atrial-ventricular conduction delay ($AR_{RV}$) between the A site and the RV site and set the $AV_{LV}$ delay based on a difference between the $AR_{RV}$ and the VV delay. The one or more processors may further be configured to measure the pacing latency PL by measuring a latency interval between a paced event, delivered at the LV site, and an evoked response, sensed at the LV site. The one or more processors may be further configured to compare the pacing latency with a threshold and adjusting the VV delay based on the comparison.

Optionally, the one or more processors may further be configured to set the interventricular pacing delay VV delay based on the conduction difference Δ and the correction term ε, and not the pacing latency PL when a difference between the IACD and $AR_{LV}$ exceeds a threshold. The one or more processors may be further configured to confirm the LUV pacing therapy using at least one of QRS related feedback, mechanical di-synchrony related feedback or stroke volume surrogate related feedback. The one or more processors may be further configured to analyze a paced QRS width in connection with multiple $AV_{LV}$ delays, and select an $AV_{LV}$ delay corresponding to the paced QRS width having a criterion of interest. The one or more processors may be further configured to analyze a contractility time delay in connection with multiple $AV_{LV}$ delays, and select an $AV_{LV}$ delay corresponding to the contractility time delay having a criteria of interest. The one or more processors may be further configured to analyze a stroke volume impedance in connection with multiple $AV_{LV}$ delays, and select an $AV_{LV}$ delay corresponding to the stroke volume impedance having a criteria of interest.

DETAILED DESCRIPTION

Figure 1:
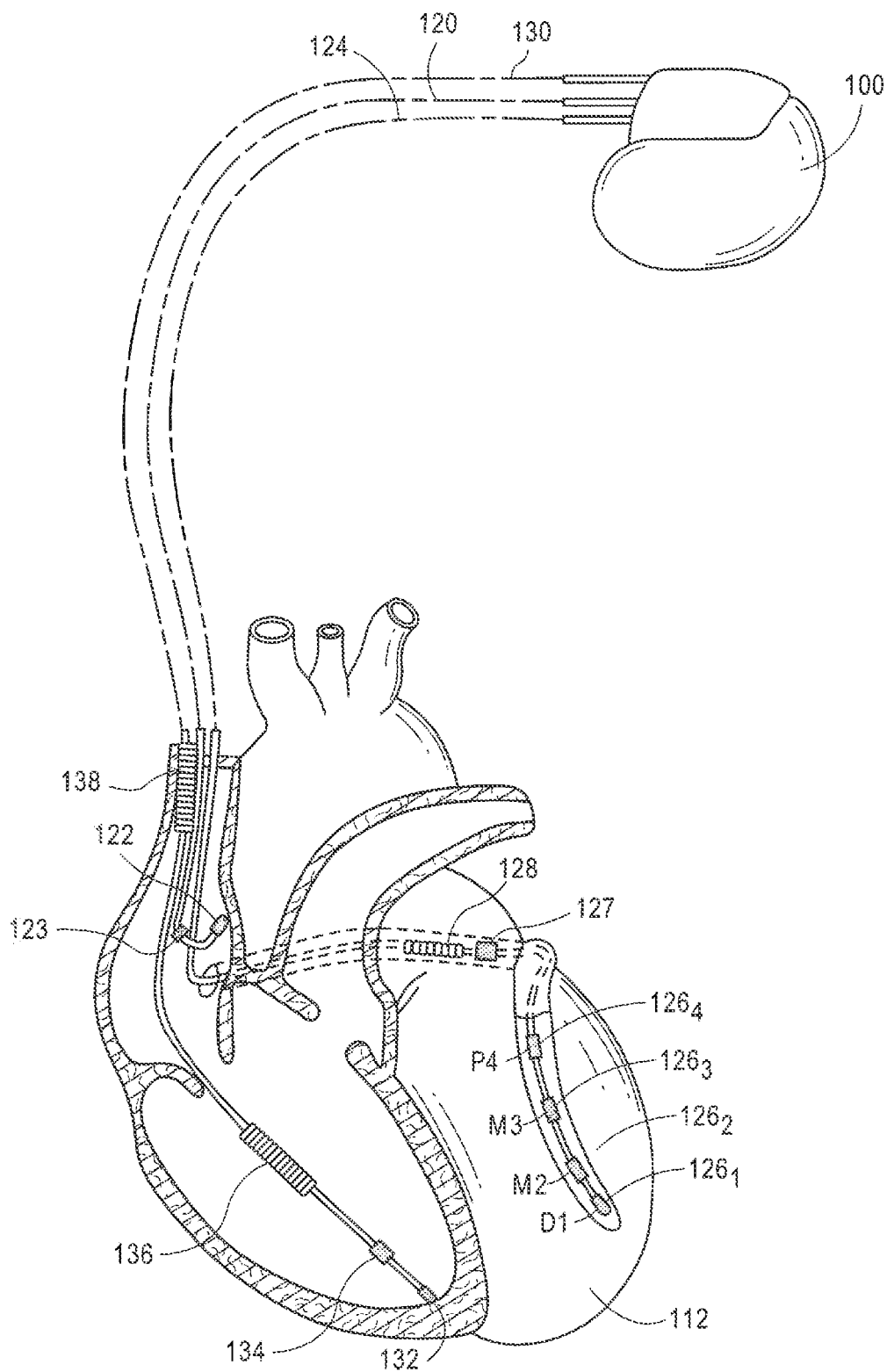
FIG. 1 illustrates an exemplary IMD formed in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "pacing/sensing electrode" refers to an electrode that is controlled and utilized by an implantable medical device and/or external programmer to perform both delivery of pacing pulses at a site and sensing of cardiac signals at the same site.

The term "non-pacing/sensing electrode" refers to an electrode that is controlled and utilized only for sensing operations. The non-pacing-sensing electrode may be on a lead coupled to a lead-based implantable medical device and/or external programmer to perform sensing of cardiac signals at the corresponding site, and is not controlled or utilized to deliver pacing pulses. The non-pacing-sensing electrode may be on a leadless implantable medical device that uses the electrode to perform sensing of cardiac signals at the corresponding site, and does not use the electrode to deliver pacing pulses.

The terms "atrial-ventricular conduction delay" and "AVCD" refer to a time interval experienced between an occurrence of an intrinsic or paced event in an atria and an occurrence of a related evoked response in a right ventricle (RV) or a left ventricle (LV). When the AVCD is measured between an atria and the RV, the resulting atrial-ventricular conduction delay to the RV is referred to as $AV_{RV}$ delay. When the AVCD is measured between an atria and the LV, the resulting atrial-ventricular conduction delay is referred to as the $AV_{LV}$ delay. For example, a conduction different $\Delta$ is determined based on a difference between i) an atrial-ventricular conduction delay ($AR_{LV}$) between the A site and the LV site, and ii) an atrial-ventricular conduction delay ($AR_{LV}$) between the A site and the RV site ($\Delta = AVCD_{LV} - AVCD_{RV}$). A correction term $\varepsilon$ is determined based on intrinsic inter-ventricular conduction delay (IVCD) between the LV and RV ($\varepsilon = IVCD_{LV} - IVCD_{RV}$).

The terms 'left monoventricular pacing". "LMV pacing", "left univentricular pacing", "LUV pacing" and "left ventricular only pacing" are used interchangeably to refer to pacing therapies that deliver pacing stimulation at one or more left ventricular sites and do not deliver any pacing stimulation to any right ventricular sites. The terms 'left monoventricular pacing", "LMV", "left univentricular pacing", "LUV" and "left ventricular only pacing" include therapies that deliver atrial pacing, but do not include biventricular pacing therapies.

Embodiments may be implemented in connection with one or more implantable medical devices (IMDs). Non-limiting examples of IMDs include one or more of implantable lead-based or leadless therapy devices. For example, the IMD may represent a pacemaker, cardioverter, cardiac rhythm management device, defibrillator, whether lead-based or leadless. For example, the IMD may include one or more structural and/or functional aspects of the device(s) described in U.S. Pat. No. 9,216,285 "Leadless Implantable Medical Device Having Removable And Fixed Components"; U.S. Pat. No. 8,442,634 "Systems and Methods for Controlling Ventricular Pacing in Patients with Long Inter-Atrial Conduction Delays"; and/or U.S. Pat. No. 8,923,965 "Systems and Methods for Optimizing AV/VV Pacing Delays Using Combined IEGM/Impedance-Based Techniques for use with Implantable Medical Devices"; U.S. Patent Application Publication 2014/0039333 "Systems and Methods for Detecting Mechanical Dyssynchrony and Stroke Volume for use with an Implantable Medical Device Employing a Multi-Pole Left Ventricular Lead", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

FIG. 1 illustrates an exemplary IMD 100 formed in accordance with embodiments herein. The IMD 100 is shown in electrical communication with a heart 112 by way of a right atrial lead 120 having an atrial tip electrode 122 and an atrial ring electrode 123 implanted in the atrial appendage. The IMD 100 is also in electrical communication with the heart by way of a right ventricular lead 130 having, in this embodiment, a ventricular tip electrode 132, a right ventricular ring electrode 134, a right ventricular (RV) coil electrode 136, and a superior vena cava (SVC) coil electrode 138. Typically, the right ventricular lead 130 is transvenously inserted into the heart so as to place the RV coil electrode 136 in the right ventricular apex, and the SVC coil electrode 138 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, IMD 100 is coupled to a multi-pole LV lead 124 designed for placement in the "CS region" via the CS OS for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 124 is designed to receive atrial and ventricular cardiac signals and to deliver left ventricular pacing therapy using a set of four left ventricular electrodes $126_1$, $126_2$, $126_3$, and $126_4$ (thereby providing a quadripole lead), left atrial pacing therapy using at least a left atrial ring electrode 127, and shocking therapy using at least a left atrial coil electrode 128 implanted on or near the left atrium. In other examples, more or fewer LV electrodes are provided. Although only three leads are shown, it should be understood that additional leads (with one or more pacing, sensing and/or shocking electrodes) might be used and/or additional electrodes might be provided on the leads already shown, such as additional electrodes on the RV lead.

Implantable Medical Device

Figure 2:
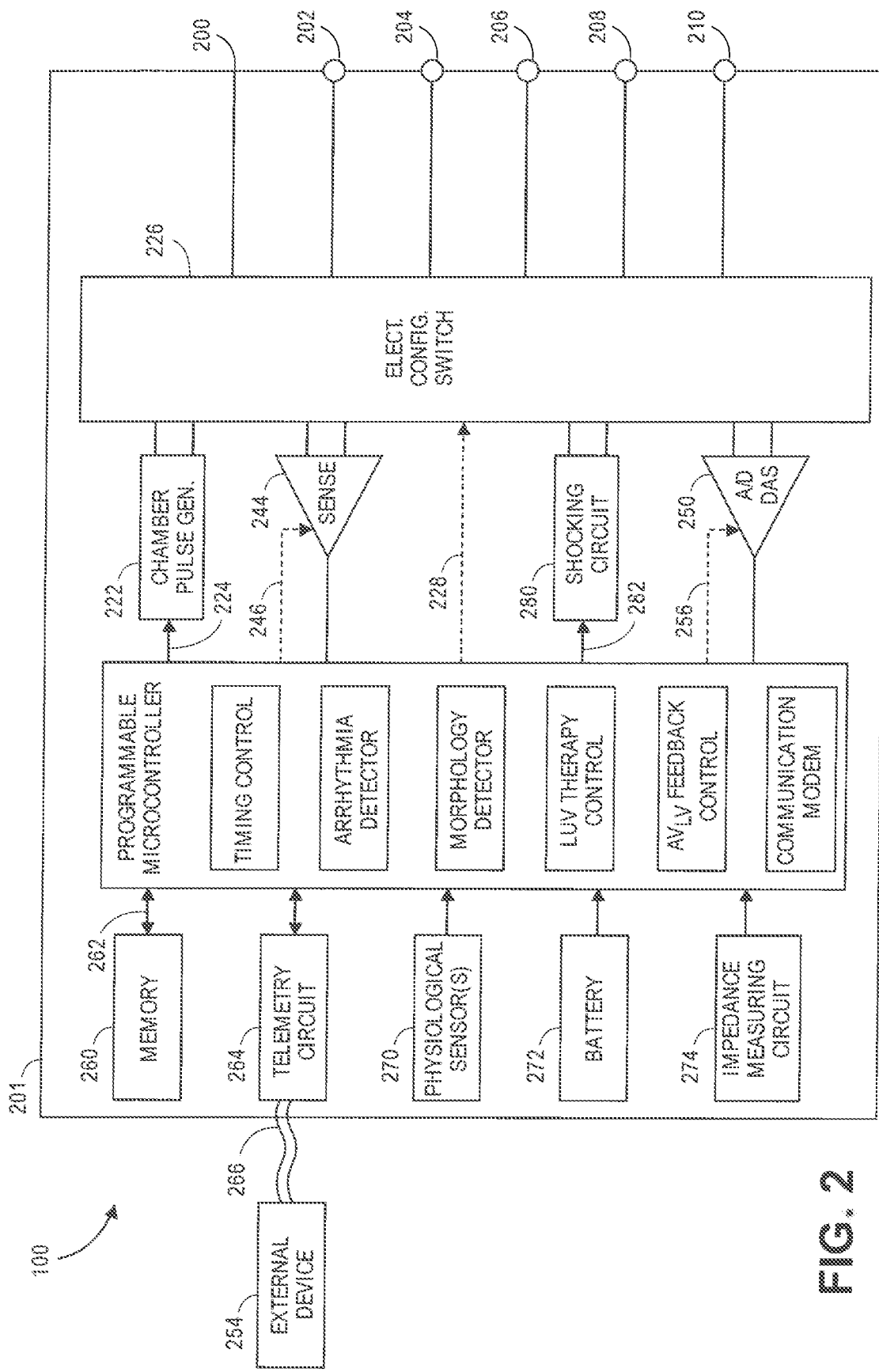
FIG. 2 shows a block diagram of an exemplary IMD that is implanted into the patient as part of the implantable cardiac system in accordance with embodiments herein.

FIG. 2 shows a block diagram of an exemplary IMD 100 that is implanted into the patient as part of the implantable cardiac system. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing. As described herein, the IMD 100 is configured to provide LUV pacing therapy without pacing the RV.

The IMD 100 has a housing 201 to hold the electronic/computing components. The housing 201 (which is often referred to as the "can", "case", "encasing", or "case electrode") may be programmably selected to act as the return electrode for certain stimulus modes. Housing 201 further includes a connector (not shown) with a plurality of terminals, a portion of which are designated as terminals 202, 204, 206, 208, and 210. The terminals may be connected to electrodes that are located in various locations within and about the heart. For example, the terminals may include: a terminal 202 to be coupled to an first electrode (e.g., a tip electrode) located in a first chamber, a terminal 204 to be coupled to a second electrode (e.g., tip electrode) located in a second chamber; a terminal 206 to be coupled to an electrode (e.g., ring) located in the first chamber; a terminal 208 to be coupled to an electrode located (e.g., ring electrode) in the second chamber; and a terminal 210 to be coupled to an electrode (e.g., coil) located in the SVC. The type and location of each electrode may vary. For example, the electrodes may include various combinations of ring, tip, coil and shocking electrodes and the like. It is understood that more or fewer terminals may be utilized. With reference to FIG. 1, the housing 201 includes at least a number of terminals corresponding to the number of electrodes provided on leads 120, 124 and 130. For example, terminals are provided to connect to the LV electrodes $126_1$-$126_4$.

The IMD 100 includes a programmable microcontroller 220 that controls various operations of the IMD 100, including cardiac monitoring and stimulation therapy. Microcontroller 220 includes a microprocessor (or equivalent control circuitry), RAM and/or ROM memory, logic and timing circuitry, state machine circuitry, and I/O circuitry.

The IMD 100 further includes one or more pulse generators 222 that generates stimulation pulses for delivery by one or more electrodes coupled thereto. The pulse generator 222 is controlled by the microcontroller 220 via control signal 224. The pulse generator 222 is coupled to the select electrode(s) via an electrode configuration switch 226, which includes multiple switches for connecting the desired electrodes to the appropriate I/O circuits, thereby facilitating electrode programmability. The switch 226 is controlled by a control signal 228 from the microcontroller 220.

In the example of FIG. 2, a single pulse generator 222 is illustrated. Optionally, the IMD 100 may include multiple pulse generators, similar to pulse generator 222, where each pulse generator is coupled to one or more electrodes and controlled by the microcontroller 220 to deliver select stimulus pulse(s) to the corresponding one or more electrodes.

Microcontroller 220 is illustrated to include timing control circuitry 232 to control the timing of the stimulation pulses (e.g., pacing rate, atrio-ventricular (AV) delay, atrial interconduction (A-A) delay, or ventricular interconduction (V-V) delay, etc.). In connection with embodiments herein, the timing control circuitry 232 is used to manage an LV atrial-ventricular ($AV_{LV}$) delay that is set as described herein to support LUV pacing therapy. The timing control circuitry 232 may also be used for the timing of refractory periods, blanking intervals, noise detection windows, evoked response windows, alert intervals, marker channel timing, and so on. Microcontroller 220 also has an arrhythmia detector 234 for detecting arrhythmia conditions and a morphology detector 236 to review and analyze one or more features of the morphology of cardiac signals.

The microcontroller 220 includes LUV therapy control circuitry 233 to implement the processes described herein for controlling an LV univentricular pacing therapy. The LUV therapy control circuitry 233 determines a conduction different Δ based on i) an atrial-ventricular conduction delay ($AR_{RV}$) between the A site and the RV site, and ii) an atrial-ventricular conduction delay ($AR_{LV}$) between the A site and the LV site. The LUV therapy control circuitry 233 determines a correction term ε based on intrinsic interventricular conduction delay (IVCD) between the LV and RV. The LUV therapy control circuitry 233 sets an LV atrial-ventricular pacing ($AV_{LV}$) delay based on the conduction difference Δ, a pacing latency PL and the correction term ε. The LUV therapy control circuitry 233 manages the LUV pacing therapy based on the $AV_{LV}$ delay, wherein the LUV pacing therapy lacks pacing in the RV.

The memory 260 is configured to store $AV_{LV}$ delay that is set by the LUV therapy control circuitry 233 based on an interventricular pacing (VV) delay that is set based on the following: VV=FCTR($\Delta*W_1+\varepsilon*W_2+PL*W_3$), where FCTR is any desired non-zero number, and $W_1$-$W_3$ represent weighting factors. The LUV therapy control circuitry 233 determines the atrial-ventricular conduction delay ($AR_{RV}$) between the A site and the RV site; and sets the $AV_{LV}$ delay based on a difference between the $AR_{RV}$ and the VV delay. The LUV therapy control circuitry 233 measures the pacing latency PL by measuring a latency interval between a paced event, delivered at the LV site, and an evoked response, sensed at the LV site. The LUV therapy control circuitry 233 compares the pacing latency with a threshold and adjusts the VV delay based on the comparison. The LUV therapy control circuitry 233 sets the interventricular pacing delay VV delay based on the conduction difference Δ and the correction term ε, and not the pacing latency PL when a difference between the IACD and $AR_{LV}$ exceeds a threshold.

The microcontroller 220 also includes $AV_{LV}$ feedback control circuitry 235 to implement the processes described in connection with FIGS. 7-11 to monitor the LUV pacing therapy and adjust the $AV_{LV}$ delay. Although not shown, the microcontroller 220 may further include other dedicated circuitry and/or firmware/software components that assist in monitoring various conditions of the patient's heart and managing pacing therapies. The $AV_{LV}$ feedback control circuitry 235 manages feedback to confirm the LUV pacing therapy. The $AV_{LV}$ feedback control circuitry 235 uses at least one of QRS related feedback, mechanical di-synchrony related feedback or stroke volume surrogate related feedback. For example, the $AV_{LV}$ feedback control circuitry 235 may analyze a paced QRS width in connection with multiple $AV_{LV}$ delays, and select an $AV_{LV}$ delay corresponding to the paced QRS width having a criteria of interest. Optionally, the $AV_{LV}$ feedback control circuitry 235 may analyze a contractility time delay in connection with multiple $AV_{LV}$ delays, and select an $AV_{LV}$ delay corresponding to the contractility time delay having a criteria of interest. Optionally, the $AV_{LV}$ feedback control circuitry 235 may analyze a stroke volume impedance in connection with multiple $AV_{LV}$ delays, and select an $AV_{LV}$ delay corresponding to the stroke volume impedance having a criteria of interest.

The IMD 100 is further equipped with a communication modem (modulator/demodulator) 240 to enable wireless communication with other devices, implanted devices and/or external devices. In one implementation, the communication modem 240 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The communication modem 240 may be implemented in hardware as part of the microcontroller 220, or as software/firmware instructions programmed into and executed by the microcontroller 220. Alternatively, the modem 240 may reside separately from the microcontroller as a standalone component.

The IMD 100 includes sensing circuitry 244 selectively coupled to one or more electrodes that perform sensing operations, through the switch 226 to detect the presence of cardiac activity in the right chambers of the heart. The sensing circuitry 244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the IMD 100 to sense low amplitude signal characteristics of atrial fibrillation. Switch 226 determines the sensing polarity of the cardiac signal by selectively closing the appropriate switches. In this way, the clinician may program the sensing polarity independent of the stimulation polarity.

The output of the sensing circuitry 244 is connected to the microcontroller 220 which, in turn, triggers or inhibits the pulse generator 222 in response to the absence or presence of cardiac activity. The sensing circuitry 244 receives a control signal 246 from the microcontroller 220 for purposes of controlling the gain, threshold, polarization charge removal circuitry (not shown), and the timing of any blocking circuitry (not shown) coupled to the inputs of the sensing circuitry.

In the example of FIG. 2, a single sensing circuit 244 is illustrated. Optionally, the IMD 100 may include multiple sensing circuit, similar to sensing circuit 244, where each sensing circuit is coupled to one or more electrodes and controlled by the microcontroller 220 to sense electrical activity detected at the corresponding one or more electrodes. The sensing circuit 244 may operate in a unipolar sensing configuration or in a bipolar sensing configuration.

The IMD 100 further includes an analog-to-digital (A/D) data acquisition system (DAS) 250 coupled to one or more electrodes via the switch 226 to sample cardiac signals across any pair of desired electrodes. The data acquisition system 250 is configured to acquire intracardiac electrogram signals, convert the raw analog data into digital data, and store the digital data for later processing and/or telemetric transmission to an external device 254 (e.g., a programmer, local transceiver, or a diagnostic system analyzer). The data acquisition system 250 is controlled by a control signal 256 from the microcontroller 220.

The microcontroller 220 is coupled to a memory 260 by a suitable data/address bus 262. The programmable operating parameters used by the microcontroller 220 are stored in memory 260 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart within each respective tier of therapy.

The operating parameters of the IMD 100 may be non-invasively programmed into the memory 260 through a telemetry circuit 264 in telemetric communication via communication link 266 with the external device 254. The telemetry circuit 264 allows intracardiac electrograms and status information relating to the operation of the IMD 100 (as contained in the microcontroller 220 or memory 260) to be sent to the external device 254 through the established communication link 266.

The IMD 100 can further include magnet detection circuitry (not shown), coupled to the microcontroller 220, to detect when a magnet is placed over the unit. A magnet may be used by a clinician to perform various test functions of the unit 200 and/or to signal the microcontroller 220 that the external programmer 254 is in place to receive or transmit data to the microcontroller 220 through the telemetry circuits 264.

The LMD 100 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. The microcontroller 220 responds by adjusting the various pacing parameters (such as rate, AV Delay, V-V Delay, etc.) at which the atrial and ventricular pacing pulses are administered. While shown as being included within the unit 200, the physiologic sensor(s) 270 may be external to the unit 200, yet still be implanted within or carried by the patient.

Examples of physiologic sensors might include sensors that, for example, sense respiration rate, pH of blood, ventricular gradient, activity, position/posture, minute ventilation (MV), and so forth.

A battery 272 provides operating power to all of the components in the IMD 100. The battery 272 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the unit 200 employs lithium/silver vanadium oxide batteries.

The IMD 100 further includes an impedance measuring circuit 274 that is enabled by the microcontroller 220 via a control signal 280. As explained herein, the impedance measuring circuit 274 may be utilized in a feedback loop to collect cardiogenic impedance signals along one or more impedance vectors while delivering an LUV pacing therapy having an $AV_{LV}$ delay defined in accordance with embodiments herein. One or more of the impedance vectors may be utilized. For example, impedance vectors may be defined between an RV electrode and a corresponding LV electrode, between and RV coil electrode and a housing/can of the IMD, and/or a combination of one or more RV electrode, one or more LV electrode and the housing/can of the IMD. The cardiogenic impedance signals may be utilized to determine contractility time delays associated with different LV sites and/or a surrogate for stroke volume. For example, the cardiogenic impedance signals may be collected as described in U.S. Pat. No. 8,923,965 "Systems and Methods for Optimizing AV/VV Pacing Delays Using Combined IEGM/Impedance-Based Techniques for use with Implantable Medical Devices"; and U.S. Patent Application Publication 2014/0039333 "Systems and Methods for Detecting Mechanical Dyssynchrony and Stroke Volume for use with an Implantable Medical Device Employing a Multi-Pole Left Ventricular Lead", which are incorporated herein by reference in their entirety.

The impedance measuring circuit 274 may also be used for: performing lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 274 is coupled to the switch 226 so that any desired electrode may be used.

The IMD 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 211 to 40 joules), as controlled by the microcontroller 220. Such shocking pulses are applied to the patient's heart 2108 through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD.

Left-Univentricular Pacing Therapy

Figure 3:
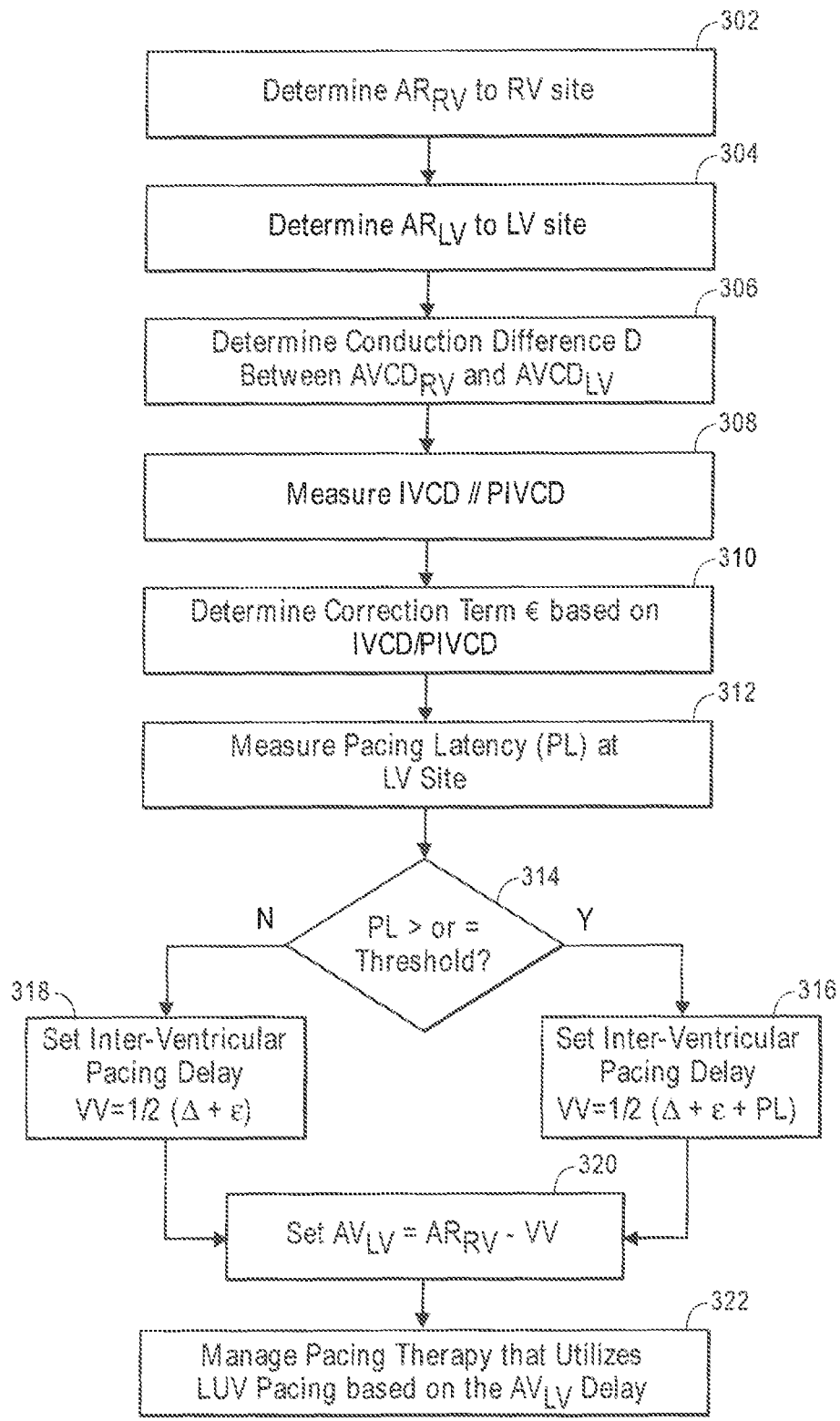
FIG. 3 illustrates a process for controlling a cardiac pacing therapy for an IMD that utilizes left mono-ventricular or left univentricular pacing in accordance with embodiments herein.

FIG. 3 illustrates a process for controlling a cardiac pacing therapy for an IMD that utilizes left mono-ventricular or left univentricular pacing in accordance with embodiments herein. All or a portion of the operations of FIG. 3 may be performed by one or more processors of an IMD, an external device, a server operating on a medical network and the like. Optionally, the operations of FIG. 3 may be implemented in combination with the systems and methods described in U.S. Pat. Nos. 8,442,634, 8,923,965 and/or U.S. Patent Application Publication 2014/0039333.

At 302, one or more processors determine an RV atrial-ventricular conduction ($AR_{RV}$) delay between an atrium (A) site and an RV site. For example, the $AR_{RV}$ delay may be measured based on an intrinsic event detected in an atrium and/or a paced event that is delivered in the atrium. By way of example, a timer may be activated when a paced or sensed event is identified in the atrium. The timer continues to operate until a corresponding intrinsic event is detected at a corresponding RV site. An example embodiment for determining the $AR_{RV}$ is described below in connection with FIG. 6.

At 304, one or more processors determine determines an LV atrial-ventricular conduction ($AR_{LV}$) delay between the A site and the LV site. For example, the $AR_{LV}$ delay may be measured based on an intrinsic event detected in an atrium and/or a paced event that is delivered in the atrium. By way of example, a timer may be activated when a paced or sensed event is identified in the atrium. The timer continues to operate until a corresponding intrinsic event is detected at a corresponding LV site.

At 306, one or more processors determine a conduction different Δ based on the RV atrial-ventricular conduction delay for the RV site ($AR_{RV}$) and based on the LV atrial-ventricular conduction delay for the LV site ($AR_{LV}$). For example, a conduction different Δ is determined based on a difference between i) an atrial-ventricular conduction delay ($AR_{LV}$) between the A site and the LV site, and ii) an atrial-ventricular conduction delay ($AR_{LV}$) between the A site and the RV site ($\Delta = AVCD_{LV} - AVCD_{RV}$). Optionally, the conduction difference Δ may be based on a weighted combination of the $AR_{RV}$ and $AR_{LV}$ (e.g., a weighted difference).

At 308, one or more processors measure an intrinsic inter-ventricular conduction delay (IVCD) and/or paced-based interventricular conduction delay (PIVCD) between the LV and RV. The interventricular conduction delay IVCD or PIVCD may be measured in either direction or in both directions based on intrinsic events sensed in the RV and LV. Optionally, the paced-based interventricular conduction delay PIVCD may be measured in either direction or both directions. For example, a paced event may be delivered in the RV, while a corresponding intrinsic event is sensed in the LV, with the delay there between corresponding to an $IVCD_{RL}$. Additionally or alternatively, a paced event may be delivered in the LV, while a corresponding intrinsic event is sensed in the RV, with the delay there between corresponding to an $TVCD_{LR}$. Optionally, the intrinsic interventricular conduction delays may be based on sensed events in both the RV and LV. One or both of the $IVCD_{RL}$ and/or $IVCD_{LR}$ may be utilized as a paced-based interventricular conduction delay.

Figure 4:
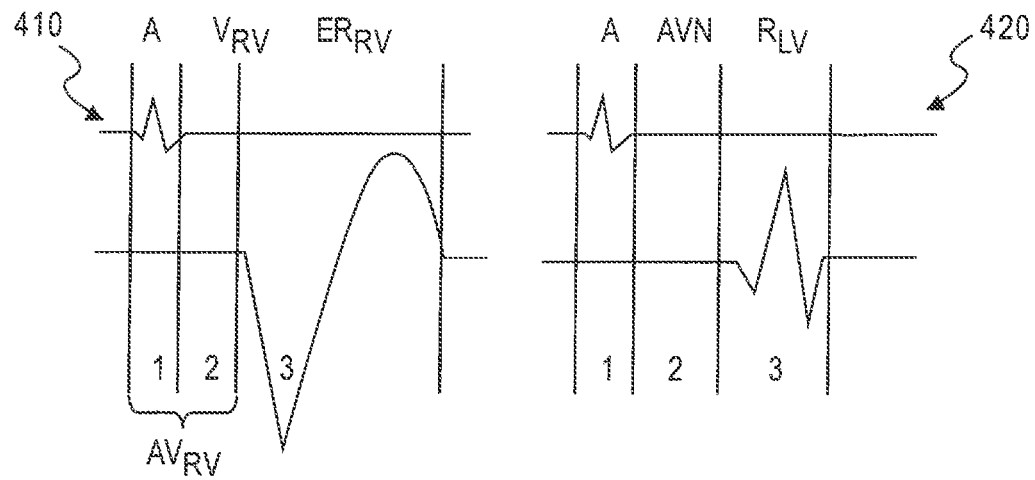
FIG. 4 illustrates example anatomical diagrams in connection with determining paced-based PIVCD in accordance with embodiments herein.
Figure 4:
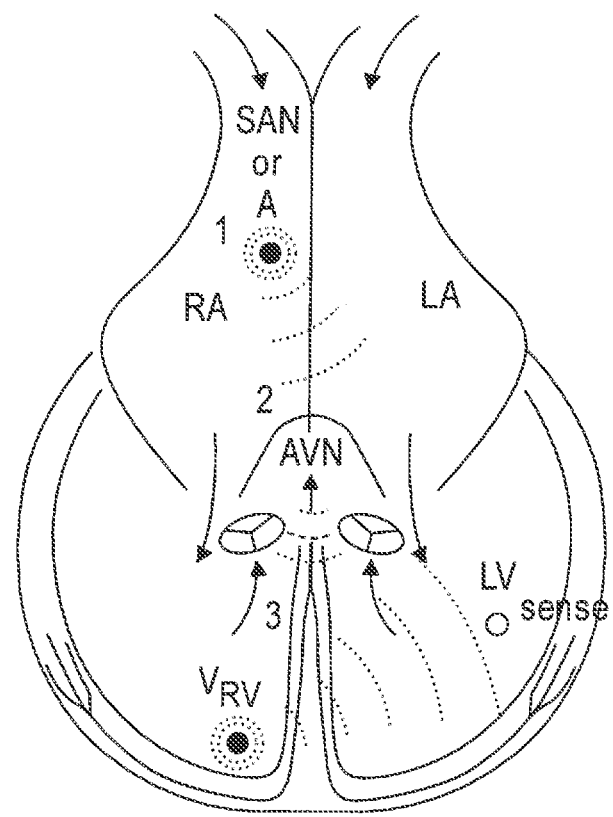
Figure 5:
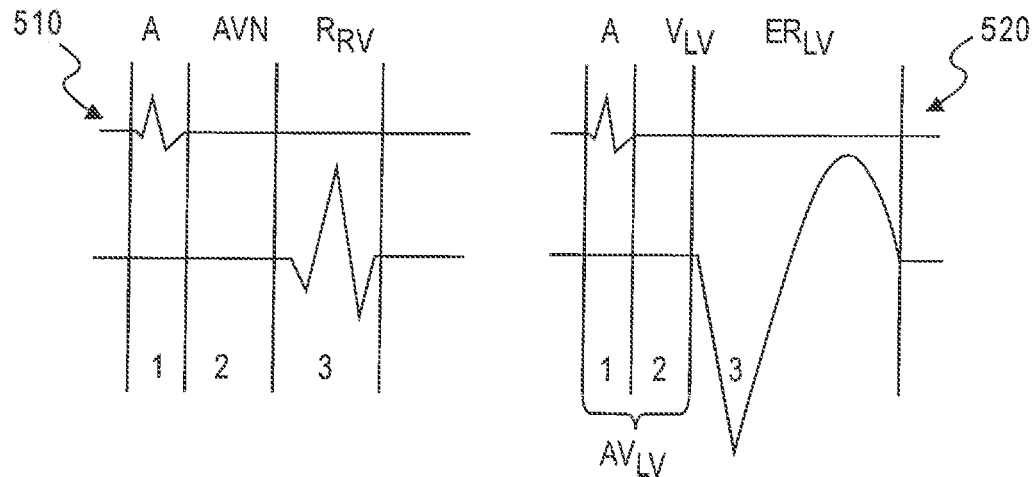
FIG. 5 illustrates example anatomical diagrams in connection with determining paced-based PIVCD in accordance with embodiments herein.
Figure 5:
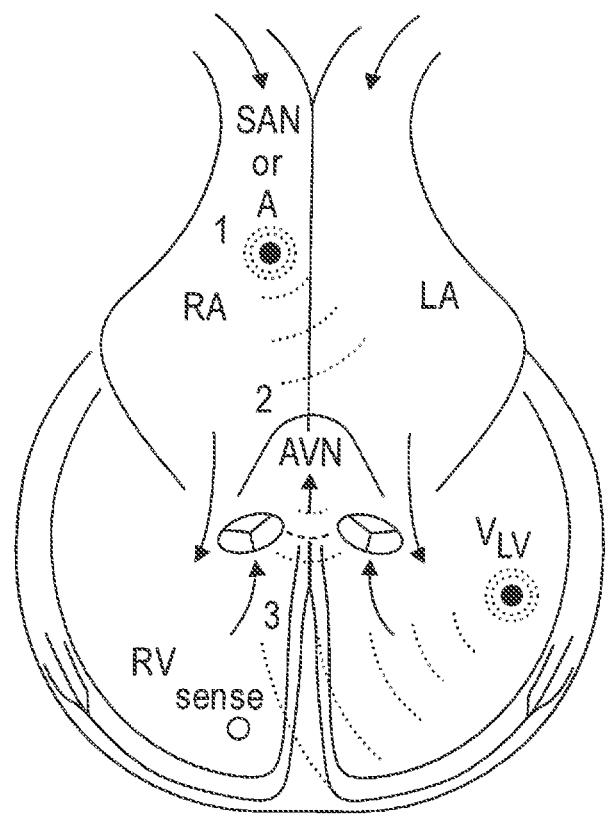

FIGS. 4 and 5 illustrate example anatomical diagrams in connection with determining paced-based PIVCD in accordance with embodiments herein. For example, the paced-based IVCD may be utilized in connection with the operation at 308-310 in FIG. 3. FIG. 4 pertains to pacing in a right ventricle and sensing in a left ventricle wherein the time between pacing and sensing is referred to as a right to left PIVCD or $PIVCD_{RL}$, which equals $R_{LV}-V_{RV}$, wherein $V_{RV}$ is a pace time of a pacing stimulus in the right ventricle and $R_{LV}$ is a sense time of a right ventricle, evoked response wavefront in the left ventricle due to the paced stimulus in the right ventricle. Thus, $PIVCD_{RL}$ is normally greater than zero. To ensure that the pacing stimulus in the right ventricle results in an evoked response, a capture routine or algorithm may be implemented. Thus, various exemplary methods, devices and/or systems include a capture algorithm (e.g., autocapture).

FIG. 4 shows a set of waveforms 410 that include an atrial event (e.g., A or P), an atrial to ventricular paced delay $AV_{RV}$, a ventricular pace time $V_{RV}$ and a sensed evoked response in the right ventricle $ER_{RV}$. Another set of waveforms 420 pertains primarily to the left ventricle and includes an atrial event (e.g., A or P), an AVN delay and a sensed evoked response in the left ventricle $R_{LV}$ which is a result of the stimulus $V_{RV}$ in the right ventricle. To ensure that the sensed evoked response in the left ventricle $R_{LV}$ is not due to conducted electrical activity from the atria, a sufficiently short ventricular paced delay $AV_{RV}$ is used. For example, a paced delay $AV_{RV}$ of approximately 30 ms to approximately 70 ms may suffice. In one example, $AV_{RV}$ is set to approximately 50 ms to approximately 80 ms. $AV_{RV}$ may also be set sufficiently short to avoid fusion. While AV is referred to, PV may also apply where appropriate.

FIG. 5 pertains to pacing in a left ventricle and sensing in a right ventricle wherein the time between pacing and sensing is referred to as a left to right PIVCD or $PIVCD_{LR}$, which equals $R_R V-V_{LV}$, wherein $V_{LV}$ is a pace time of a pacing stimulus in the left ventricle and $R_{RV}$ is a sense time of a left ventricle, evoked response wavefront in the right ventricle due to the paced stimulus in the left ventricle. Thus, $PIVCD_{LR}$ is normally greater than zero. To ensure that the pacing stimulus in the left ventricle results in an evoked response, a capture routine or algorithm may be implemented. Thus, various exemplary methods, devices and/or systems include a capture algorithm (e.g., autocapture).

FIG. 5 shows a set of waveforms 520 that includes an atrial event (e.g., A or P), an atrial to ventricular paced delay $AV_{LV}$, a ventricular pace time $V_{LV}$ and a sensed evoked response in the left ventricle $ER_{LV}$. Another set of waveforms 510 pertains primarily to the right ventricle and includes an atrial event (e.g., A or P), an AVN delay and a sensed evoked response in the right ventricle $R_{RV}$ which is a result of the stimulus $V_{LV}$ in the left ventricle. To ensure that the sensed evoked response in the right ventricle $R_{RV}$ is not due to conducted electrical activity from the atria, a sufficiently short ventricular paced delay $AV_{LV}$ is used. For example, a paced delay $AV_{LV}$ of approximately 30 ms to approximately 70 ms may suffice. In one example, $AV_{LV}$ is set to approximately 50 ms to approximately 80 ms. $AV_{LV}$ may also be set sufficiently short to avoid fusion. While AV is referred to, PV may also apply where appropriate.

Returning to FIG. 3, after the measurement at 308, flow moves to 310. At 310, one or more processors determine a correction term ε based on the intrinsic interventricular conduction delay IVCD or paced-based interventricular delay PIVCD. For example, the correction term ε is determined based on a difference in an intrinsic inter-ventricular conduction delay (IVCD) between the LV and RV ($\varepsilon=IVCD_{LV}-IVCD_{RV}$). Optionally, the correction term $\varepsilon$ may be based on a weighted difference between the PIV-$CD_{RL}$ and $IVCD_{LR}$.

At 312, one or more processors measure a pacing latency (PL) at the LV site. For example, the pacing latency PL is measured by measuring a latency interval between a paced event delivered at an LV site and an evoked response sensed at the same LV site. In the present example, the measurement at 312 is shown to be performed during the operations of FIG. 3. However, optionally, the measurement at 312 may be performed at any time independent of, separate from and/or in parallel with the other operations of FIG. 3. For example, pacing latency may be determined at any point within delivery of a pacing therapy, such as following any LV pacing event. The pacing latency may be recorded for future use during the process of FIG. 3.

At 314, one or more processors determine whether the pacing latency equals or exceeds a threshold. The threshold may set programmed by a clinician, or set automatically by the IMD based on feedback obtained during operation. By way of example, the threshold may be 5 msec, 10 msec, etc. Optionally, the threshold may be dynamically adjusted based on the patient's physiologic behavior, such as the resting heart rate, current heart rate, activity level, and the like. When the pacing latency equals or exceeds the threshold, flow advances to 316. When the pacing latency falls below the threshold, flow advances to 318.

At 316, the one or more processors set an interventricular pacing (VV) delay based on a weighted combination of the conduction difference $\Delta$, the pacing latency PL and the correction term $\varepsilon$. For example, the interventricular pacing delay may be set based on the equation: $VV=\frac{1}{2}*(\Delta+\varepsilon+PL)$. Optionally, different weights may be applied to the parameters $\Delta$, $\varepsilon$ and PL, before combining the parameters. For example, the interventricular pacing delay may be set based on the general equation: $VV=FCTR*(\Delta*W_1+\varepsilon*W_2+PL*W_3)$, where FCTR is any desired non-zero number, and $W_1$-$W_3$ represent weighting factors for the corresponding parameters. In the foregoing example, the pacing latency is subtracted from the delay VV. Optionally, pacing latency may be added to the difference $\Delta$ and correction term $\varepsilon$ to derive the VV delay.

At 318, the one or more processors set the VV delay based on the combination of the conduction difference $\Delta$ and the correction term $\varepsilon$. The setting operation at 318 is not based on the pacing latency. For example, the interventricular pacing delay may be set based on the equation: $VV=\frac{1}{2}*(\Delta+\varepsilon)$, without regard for pacing latency. Optionally, different weights may be applied to the parameters $\Delta$ and $\varepsilon$, before combining the parameters. For example, the interventricular pacing delay may be set based on the general equation: $VV=FCTR*(\Delta*W_1+\varepsilon*W_2)$, where FCTR is any desired non-zero number, and $W_1$-$W_2$ represent weighting factors for the corresponding parameters.

At 320, the one or more processors set the LV atrial ventricular pacing delay AVLV based on the RV atrial ventricular conduction delay AVRV and the VV delay. For example, the LV atrial-ventricular pacing delay may be set to equal the RV atrial ventricular conduction delay minus the VV delay. Optionally, one or more weighting factors may be applied to the RV atrial ventricular conduction delay and the VV delay.

At 322, the one or more processors manage a pacing therapy that includes left univentricular (LUV) pacing that utilizes the LV atrial ventricular pacing delay AVLV. In particular, when a paced or sensed atrial event occurs, the IMD sets a timer corresponding to the LV atrial-ventricular pacing delay AVLV. If the timer corresponding to the LV atrial-ventricular pacing delay AVLV times out before an intrinsic ventricular event is sensed in the LV, the IMD delivers a pacing stimulation to one or more LV sites corresponding to the LUV pacing. In accordance with the process of FIG. 3, the pacing therapy does not pace in the RV. It is recognized that the pacing therapy determined in accordance with the operations of FIG. 3 may perform atrial pacing.

Figure 6:
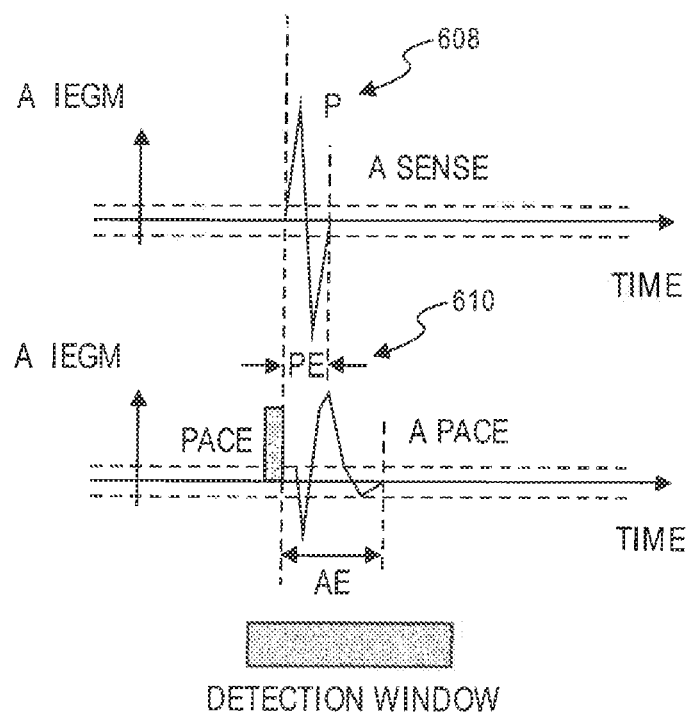
FIG. 6 illustrates a diagram to describe a process for determining an RV atrial-ventricular conduction delay ($AR_{RV}$) between an atrium (A) site and an RV site in accordance with embodiments herein.

FIG. 6 illustrates a diagram to describe a process for determining an RV atrial-ventricular conduction delay ($AR_{RV}$) between an atrium (A) site and an RV site in accordance with embodiments herein. One or more processors measure an inter-atrial conduction (A-A) delay (also referred to herein as IACT delay), and determine an AV/PV pacing delay based on the measured inter-atrial (A-A) conduction delays. Optionally, the inter-atrial conduction delays may be estimated based on the duration of atrial events, i.e. the duration of P-waves or atrial evoked responses. The duration of the P-wave is referred to herein as PE. The duration of the atrial evoked response is referred to herein as AE. Additional information regarding the determination and exploitation of inter-atrial conduction delays is set forth in U.S. Pat. No. 7,248,925, cited above. Herein, inter-atrial delays refer to delays measured between two points on or within one or both of the atria. In the exemplary embodiments described herein, one point is on or within the left atrium and the other is on or within the right atrium; however, other embodiments may involve measurements taken between two points on or within one atrial chamber. Accordingly, these inter-atrial delays may alternatively be referred to as intra-atrial delays.

In FIG. 6, a P-wave 608 is illustrated to have a duration PE and an atrial evoked response 610 is illustrated to have a duration AE. A detection window may be used to detect P-waves and/or atrial evoked responses, as shown. The detection window ends at the ventricular event (either V sensed or V paced event). FIG. 6 also provides formula for determining PV based on PE, and for determining AV based on AE, as follows:

$$AV=AE+\delta;\ \text{if}\ AE<150\ \text{ms},\ \delta=60\ \text{ms};\ \text{if}\ AE\geq150\ \text{ms},\ \delta=30\ \text{ms}.$$

$$PV=PE+\delta;\ \text{if}\ PE<100\ \text{ms},\ \delta=60\ \text{ms};\ \text{if}\ PE\geq100\ \text{ms},\ \delta=30\ \text{ms}.$$

More generally, for AV delays, $\delta$ is set to a first programmable or hard-coded offset value ($T_1$) if AE is at least equal to a programmable threshold ($TH_{AE}$) and is instead set to a second programmable value ($T_2$) if AE is less than $TH_{AE}$. In the example shown, $T_1$ is 30 milliseconds (ms), $T_2$ is 60 ms, and $TH_{AE}$ is 150 ms. Although these values are typically preferred, other suitable values for $T_1$, $T_2$, and $TH_{AE}$ may potentially be used as determined, e.g., via otherwise routine experimentation. Likewise, for PV delays, $\delta$ is set to a first programmable value ($T_1$) if PE is at least equal to $TH_{PE}$ and is instead set to a second programmable value $T_2$ if PE is less than $TH_{PE}$. In the example shown, $T_1$ is again 30 ms and $T_2$ is 60 ms. $TH_{PE}$ is 100 ms. Although these values are typically preferred, other suitable values for $T_1$, $T_2$, and $VV_{PE}$ may potentially be used as determined, e.g., via otherwise routine experimentation. Also, the $T_1$ and $T_2$ use for calculating AV may differ from those used for calculating PV.

Figure 7:
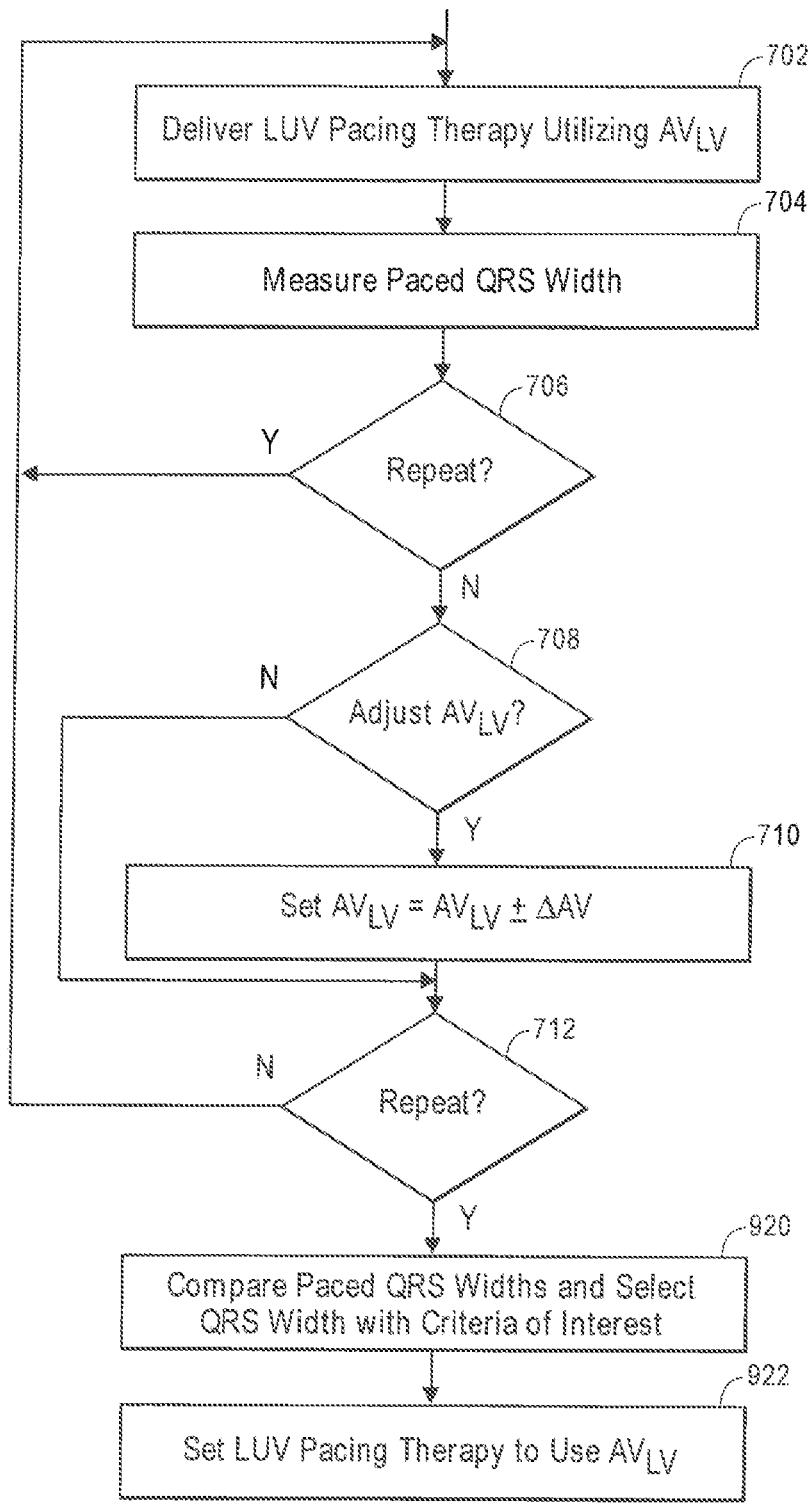
FIG. 7 illustrates a process for confirming an LUV pacing therapy through the use of QRS-related feedback in accordance with embodiments herein.

FIG. 7 illustrates a process for confirming an LUV pacing therapy through the use of QRS-related feedback in accordance with embodiments herein. Beginning at 702, the one or more processors deliver an LUV therapy that utilizes an $AV_{LV}$ delay calculated in accordance with embodiments herein, based at least in part on pacing latency). At 704, the one or more processors measure and save a paced QRS width corresponding to the width of the QRS complex in connection with a paced event. At 706, the one or more processors determine whether to continue delivering the LUV pacing therapy and measuring the paced QRS width. If so, flow returns to 702. Otherwise, flow advances to 708. For example, a select number of paced events may be delivered at 702 and a select number of paced QRS widths may be measured and saved at 704 before it is desirable to continue the process. The paced QRS widths measured and saved at 704 may be combined to form an average or separately stored for individual analysis in connection here with. Optionally, the process at 702-704 may be repeated for a predetermined period of time or predetermined number of cardiac cycles or the like.

At 708, the one or more processors determine whether to adjust to the $AV_{LV}$ delay. When it is desirable to adjust the $AV_{LV}$ delay, flow advances to 710. At 710, the $AV_{LV}$ delay is adjusted by a predetermined $AV_{LV}$ delay increment, such as a programmed amount or automatically determined amount. For example, the $AV_{LV}$ delay increment may be set to 5 msec, 10 msec, and the like with the $AV_{LV}$ delay being increased or decreased by the corresponding $AV_{LV}$ delay increment during each iteration at 710. Returning to 708, when no adjustment in the $AV_{LV}$ delay is desired, the operation at 710 is skipped.

At 712, the one or more processors determine whether to repeat the operations at 702-710. When the process is to be repeated, flow returns to 702, otherwise flow continues to 714. At 714, the one or more processors compare the saved paced QRS widths to determine a desired one of the paced QRS widths that has a criteria of interest. For example, the criteria of interest may correspond to the shortest QRS width. Optionally, the criteria of interest may correspond to a QRS width within a desired length. Additional and alternative criteria of interest may be applied when selecting the paced QRS width. At 714, the one or more processors select the QRS width that has the criteria of interest and determine the corresponding associated $AV_{LV}$ delay. At 716, the one or more processors update the LUV pacing therapy to use the $AV_{LV}$ delay determined at 714.

In accordance with the process of FIG. 7, a feedback loop is provided to monitor physiologic response to the programmed $AV_{LV}$ delay parameter for an LUV pacing therapy. Additionally or alternatively, additional parameters may be adjusted at 708-710 and analyzed at 714 in connection with utilizing the feedback loop to review the physiologic response to the LUV pacing therapy.

Figure 8:
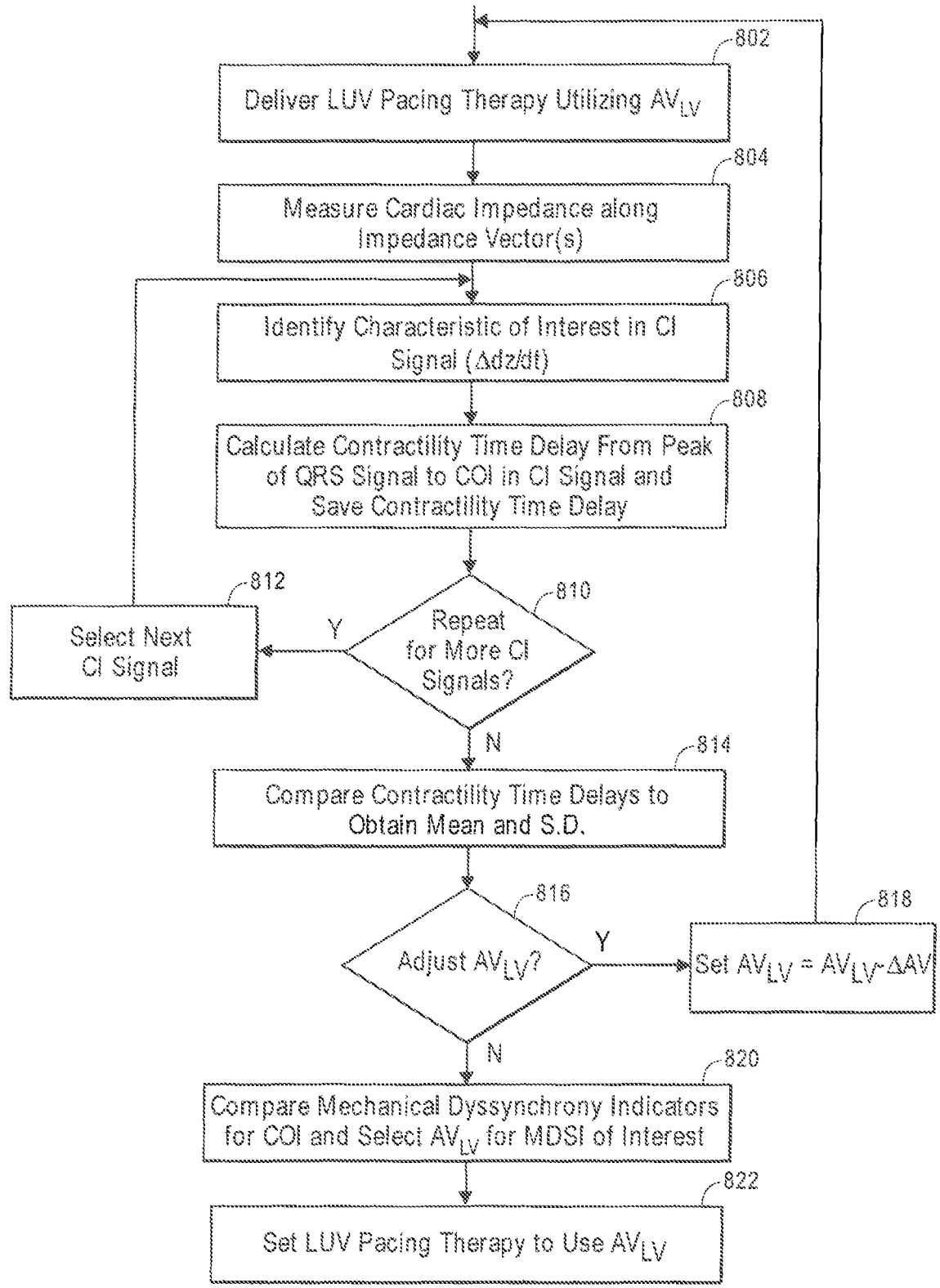
FIG. 8 illustrates a process for confirming an LUV pacing therapy through the use of mechanical dyssynchrony related feedback in accordance with embodiments herein.

FIG. 8 illustrates a process for confirming an LUV pacing therapy through the use of mechanical dyssynchrony related feedback in accordance with embodiments herein. Beginning at 802, the one or more processors deliver an LUV therapy that utilizes an $AV_{LV}$ delay calculated in accordance with embodiments herein, based at least in part on pacing latency).

At 804, the one or more processors measure and save cardiogenic impedance signals along one or more impedance vectors through the LV. For example, an impedance vector may be between an electrode located at an RV site (e.g., an RV coil electrode) and an electrode located at an LV site. Optionally, when electrodes are positioned at multiple LV sites, separate cardiogenic impedance signals may be obtained for impedance vectors associated with each of the LV sites, and/or combinations of the LV sites. For example, the lead may include four LV electrodes (e.g., a proximal electrode, first middle electrode, second middle electrode and distal electrode). First cardiogenic impedance measurements may be obtained along a first impedance vector between the proximal LV electrode and an RV electrode. Second cardiogenic impedance measurements may be obtained along a second impedance vector between the first middle electrode and the RV electrode, while third and fourth cardiogenic impedance measurements may be obtained along a third impedance vector (second middle electrode to RV electrode) and along a fourth impedance vector (distal electrode to RV electrode). Additionally or alternatively, combinations of the LV sites may be combined to form a virtual LV electrode, with the impedance vector extending between the RV electrode and the virtual LV electrode.

At 806, the one or more processors analyze a cardiogenic impedance (CI) signal corresponding to the cardiogenic impedance measurements collected along one impedance vector. The processors identify an impedance characteristic of interest from the CI signal. For example, the impedance characteristic of interest (COI) may correspond to a maximum or minimum in the slope of the CI signal over time (e.g., maximum $\Delta dZ/dt$). At 808, the one or more processors determine a contractility time delay between a QRS complex COI and the impedance COI. For example, the QRS complex COI may correspond to the peak of the QRS complex, while the impedance COI corresponds to the maximum slope in the CI signal. The contractility time delay between the characteristics of interest is saved at 808. At 810, the processor determines whether additional CI signals are to be analyzed. When additional CI signals are to be analyzed, flow moves to 812. At 812, the next CI signal is selected. Thereafter, the operations at 806-810 are repeated for one or more CI signals measured in connection with an impedance vector between an RV electrode and a present LV electrode. The operations at 806-810 may be repeated for impedance vectors associated with multiple LV electrodes. Continuing with the foregoing example, when a lead includes four LV electrodes, it may be desirable to measure CI signals along four separate impedance vectors (between the corresponding LV electrodes and a common RV electrode). The operations at 806-810 obtain contractility time delays associated with LV sites where the LV electrodes are located. Returning to 810, when no more CI signals are to be analyzed, flow continues to 814.

At 814, the one or more processors compare the contractility time delays associated with the different LV electrodes/sites to identify a mechanical dyssynchrony indicator there between. For example, the contractility time delays associated with a different LV electrodes/sites may be analyzed to identify a mean and a standard deviation there between. A large standard deviation may represent a mechanical dyssynchrony indicator as the maximum change in the impedance COI occurs at a different point in time at each of the LV sites. When the LV exhibits mechanical synchrony (or low mechanical dyssynchrony), the impedance COI may be expected to exhibit a maximum $\Delta dZ/dt$ at approximately the same point in time for each of the LV sites. While the present example utilizes mean and standard deviation as the measure of differences in the contractility time delays for the different LV electrodes, it is recognized that another timing characteristic may be analyzed additionally or alternatively.

At 816, the one or more processors determine whether to adjust to the $AV_{LV}$ delay. When it is desirable to adjust the $AV_{LV}$ delay, flow advances to 818. At 818, the $AV_{LV}$ delay is adjusted by a predetermined $AV_{LV}$ delay increment, such as a programmed amount or automatically determined amount. For example, the $AV_{LV}$ delay increment may be set to 5 msec, 10 msec, and the like with the $AV_{LV}$ delay being increased or decreased by the corresponding $AV_{LV}$ delay increment during each iteration at 818. Returning to 816, when no adjustment in the $AV_{LV}$ delay is desired, flow continues to 820. The operations at 802-818 are repeated in connection with multiple $AV_{LV}$ delay, to obtain a collection of $AV_{LV}$ delays, each of which has a corresponding mechanical dyssynchrony indicator (e.g., corresponding to a mean and standard deviation in the contractility time delays for the different LV electrodes/sites.

At 820, the one or more processors compare the saved mechanical dyssynchrony indicators (MDSI) to determine a desired one of the mechanical dyssynchrony indicators that has a criteria of interest. For example, the criteria of interest may correspond to a minimum standard deviation between the contractility time delays associated with an $AV_{LV}$ delay. Optionally, the criteria of interest may correspond to a combination of contractility time delays within a desired range of one another. Additional and alternative criteria of interest may be applied when selecting the mechanical dyssynchrony indicator. At 820, the one or more processors select the MDSI that has the criteria of interest and determine the corresponding $AV_{LV}$ delay. At 822, the one or more processors update the LUV pacing therapy to use the $AV_{LV}$ delay determined at 820.

In accordance with the process of FIG. 8, a feedback loop is provided to monitor mechanical dyssynchrony indicators in response to the programmed $AV_{LV}$ delay parameter for an LUV pacing therapy.

Figure 9:
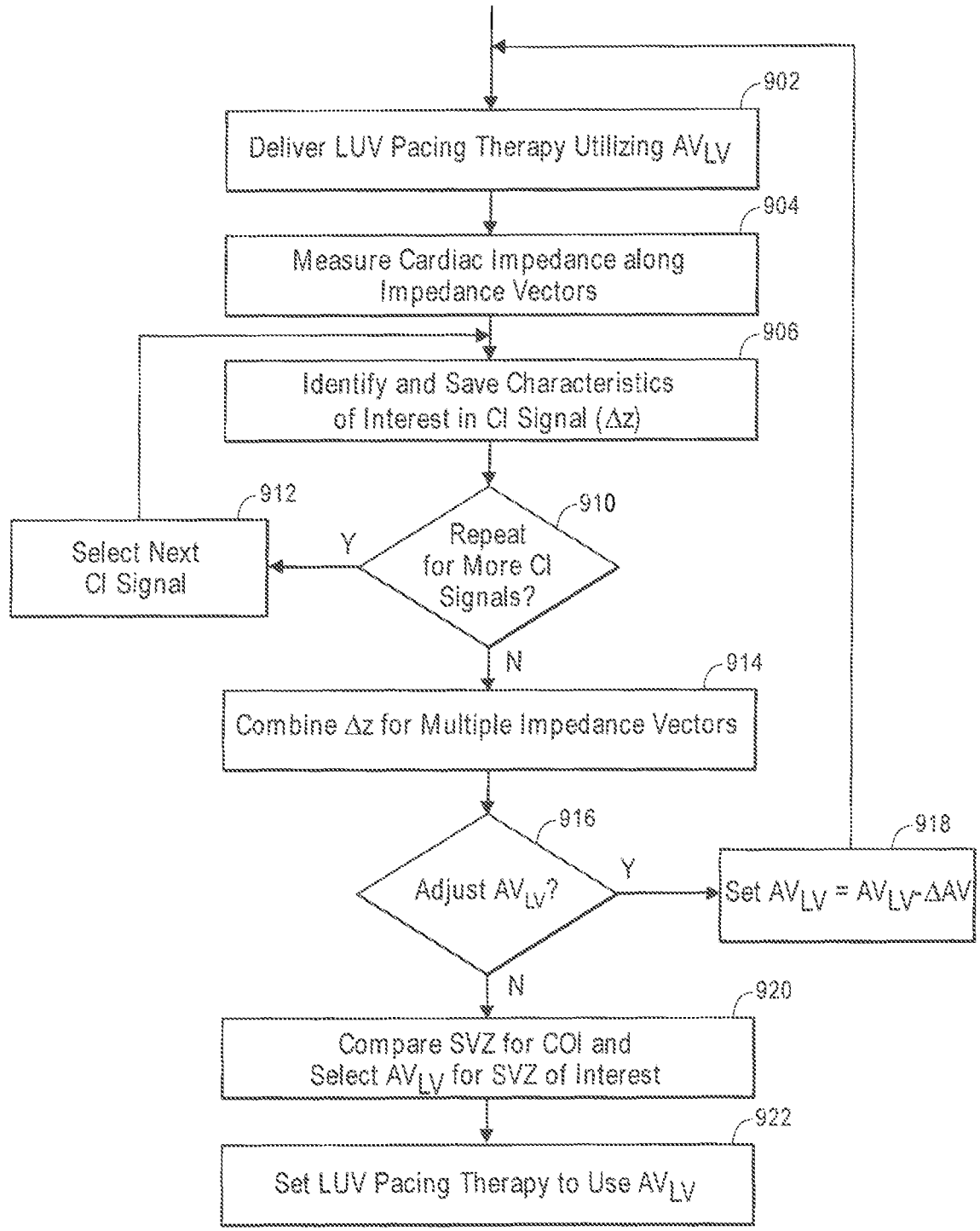
FIG. 9 illustrates a process for confirming an LUV pacing therapy through the use of stroke volume related feedback in accordance with embodiments herein.

FIG. 9 illustrates a process for confirming an LUV pacing therapy through the use of stroke volume related feedback in accordance with embodiments herein. Beginning at 902, the one or more processors deliver an LUV therapy that utilizes an $AV_{LV}$ delay calculated in accordance with embodiments herein.

At 904, the one or more processors measure and save cardiogenic impedance measurements along one or more impedance vectors. For example, an impedance vector may be between an electrode located at an RV site (e.g., an RV coil electrode) and an electrode located at an LV site. Optionally, when electrodes are positioned at multiple LV sites, separate cardiogenic impedance measurements may be obtained for impedance vectors associated with each of the LV sites, and/or combinations of the LV sites. For example, the lead may include four LV electrodes (e.g., a proximal electrode, first middle electrode, second middle electrode and distal electrode). First cardiogenic impedance measurements may be obtained along a first impedance vector between the proximal LV electrode and an RV electrode. Second cardiogenic impedance measurements may be obtained along a second impedance vector between the first middle electrode and the RV electrode, while third and fourth cardiogenic impedance measurements may be obtained along a third impedance vector (second middle electrode to RV electrode) and along a fourth impedance vector (distal electrode to RV electrode). Additionally or alternatively, combinations of the LV sites may be combined to form a virtual LV electrode, with the impedance vector extending between the RV electrode and the virtual LV electrode.

As described above in connection with FIG. 8, the impedance vectors may extend between an RV electrode and an LV electrode. Additionally or alternatively, the impedance vector may extend between an RV electrode and the can or housing of the IMD. Additionally or alternatively, the impedance vector may extend between an RV electrode, and LV electrode and the housing or can of the IMD.

At 906, the one or more processors analyze a cardiogenic impedance (CI) signal corresponding to the cardiogenic impedance measurements collected along one impedance vector. The processors identify one or more impedance characteristics of interest from the CI signal. For example, the impedance characteristic of interest (COI) may correspond to an impedance difference ($\Delta Z$) between maximum and minimum impedance levels exhibited by the CI signal. The impedance difference $\Delta Z$ is saved at 906. At 910, the processor determines whether additional CI signals are to be analyzed. When additional CI signals are to be analyzed, flow moves to 912. At 912, the next CI signal is selected. Thereafter, the operation at 906 is repeated for the next CI signal. The operation at 906 is repeated for impedance vectors associated with multiple LV electrodes. Continuing with the foregoing example, when a lead includes four LV electrodes, it may be desirable to analyze impedance differences for the CI signals along four separate impedance vectors. At 910, when no more CI signals are to be analyzed, flow continues to 914.

At 914, the one or more processors combined the impedance differences AZ identified for multiple impedance vectors to obtain a stroke volume surrogate (e.g., a maximum stroke volume impedance). For example the impedance differences may be summed for the multiple impedance vectors to obtain a stroke volume impedance (SVZ). A large stroke volume impedance may represent a large stroke volume, a small stroke volume impedance may represent a smaller stroke volume. Optionally, the impedance differences may be combined in various manners to obtain the stroke volume impedance. Optionally, a subset of the CI signals may be utilized to derive the stroke volume impedance.

At 916, the one or more processors determine whether to adjust to the $AV_{LV}$ delay. When it is desirable to adjust the AVLV delay, flow advances to 918. At 918, the AVLV delay is adjusted by a predetermined $AV_{LV}$ delay increment, such as a programmed amount or automatically determined amount. When no adjustment in the $AV_{LV}$ delay is desired, flow continues to 920. The operations at 902-918 are repeated in connection with multiple $AV_{LV}$ delay, to obtain a collection of $AV_{LV}$ delays, each of which has a corresponding stroke volume impedance.

At 920, the one or more processors compare the saved stroke volume impedances to determine a desired one of the stroke volume impedances that has a criteria of interest. For example, the criteria of interest may correspond to a maximum stroke volume impedance associated with an $AV_{LV}$ delay. Additional and alternative criteria of interest may be applied when selecting the SVZ. At 920, the one or more processors select the SVZ that has the criteria of interest and determine the corresponding $AV_{LV}$ delay. At 922, the one or more processors update the LUV pacing therapy to use the $AV_{LV}$ delay determined at 920.

In accordance with the process of FIG. 9, a feedback loop is provided to monitor stroke volume impedance in response to the programmed AVLV delay parameter for an LUV pacing therapy. By way of example, the processes of FIGS. 8 and 9 may measure and analyze CI signals as described in U.S. Pat. No. 8,923,965 and/or U.S. Patent Application Publication 2014/0039333.

Figure 10:
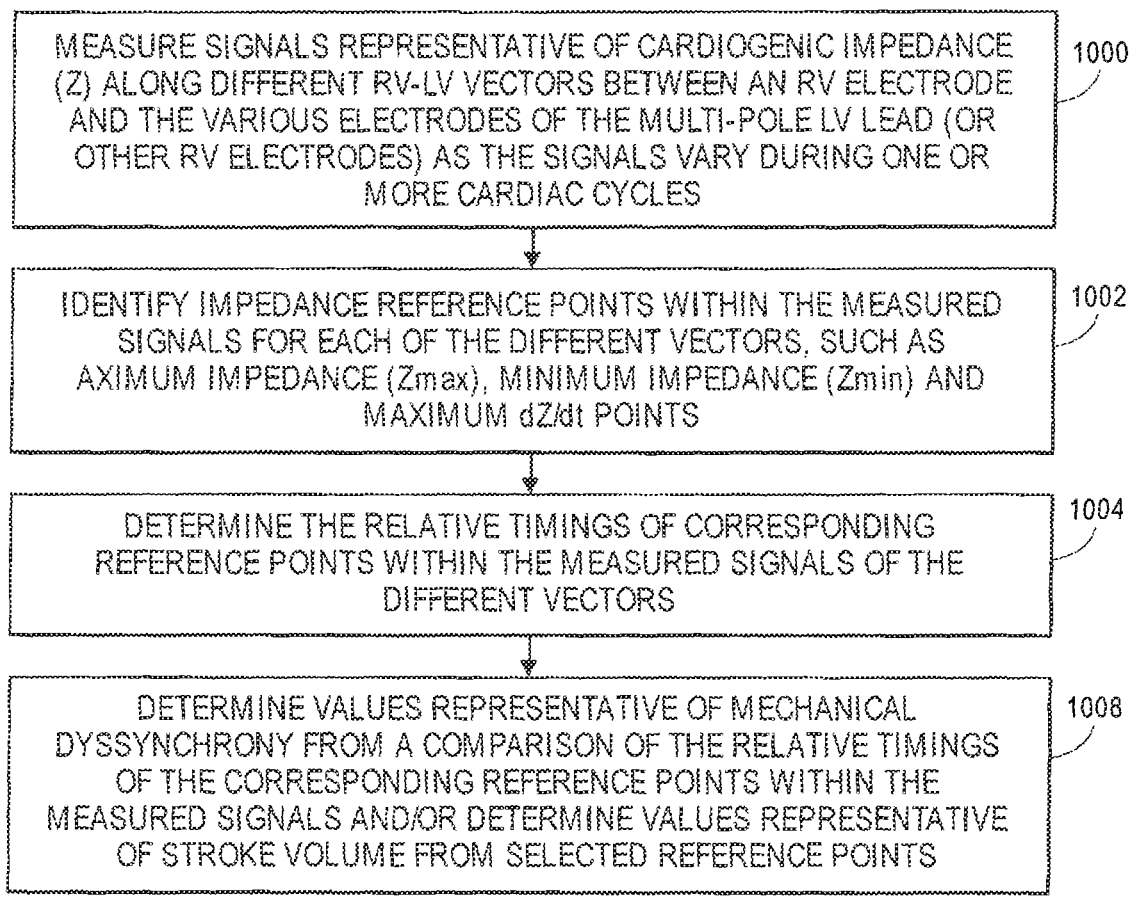
FIG. 10 illustrates a method for assessing mechanical dyssynchrony and stroke volume based on cardiogenic impedance that may be implemented in connection with the processes of FIGS. 8-9 in accordance with embodiments herein.

FIG. 10 illustrates a method for assessing mechanical dyssynchrony and stroke volume based on cardiogenic impedance that may be implemented in connection with the processes of FIGS. 8-9 in accordance with embodiments herein. The operations of FIG. 10 represent an example implementation of the operations 804-814 in FIG. 8 and/or the operations at 904-914 in FIG. 9. The operations of FIG. 10 may be implemented by one or more processors of an IMD and/or an external device. At 1000, the one or more processors measures signals representative of cardiogenic impedance (such as impedance (Z), admittance, conductance (C) or emittance) along different RV-LV vectors between an RV electrode (such as the RV coil) and the various electrodes of the multi-pole LV lead as the signals vary during one or more cardiac cycles. That is, a set of time-varying impedance signals Z(t) are measured, with one Z(t) signal measured for each of the different RV-LV vectors. For a quadripolar LV lead, four RV-LV vectors are thereby measured, yielding four corresponding Z(t) signals, denoted $Z_1$, $Z_2$, $Z_3$ and $Z_4$ (or $C_1$, $C_2$, $C_3$, and $C_4$). Note that various RV-RV impedance vectors may also be exploited such as by injecting current RV coil to LV tip and then sensing voltage RV tip or RV ring to RV coil. At step 1002, the device identifies reference points (or fiducial points) within the measured Z signals for each of the different RV-LV vectors (and/or any RV-RV impedance vectors that are used), such as maximum impedance (Zmax), minimum impedance (Zmin) and max dZ/dt points. Hence, in one example, each separate impedance vector (e.g., $Z_1$) yields a pair of Zmax and Zmin values (e.g., $Z_1$ max and $Z_1$ min) for a given cardiac cycle, as well as a max dZ/dt value. At step 1004, the device determines the relative timings of corresponding reference points within the measured signals of the different RV-LV vectors (and/or any RV-RV impedance vectors that are used). For example, the device determines the time (t1) of the Zmax value of the first vector, the time (t2) of the Zmax value of the second vector, and so on. Likewise, the device determines the time (t1') of the Zmin value of the first vector, the time (t2') of the Zmin value of the second vector, and so on.

Figure 11:
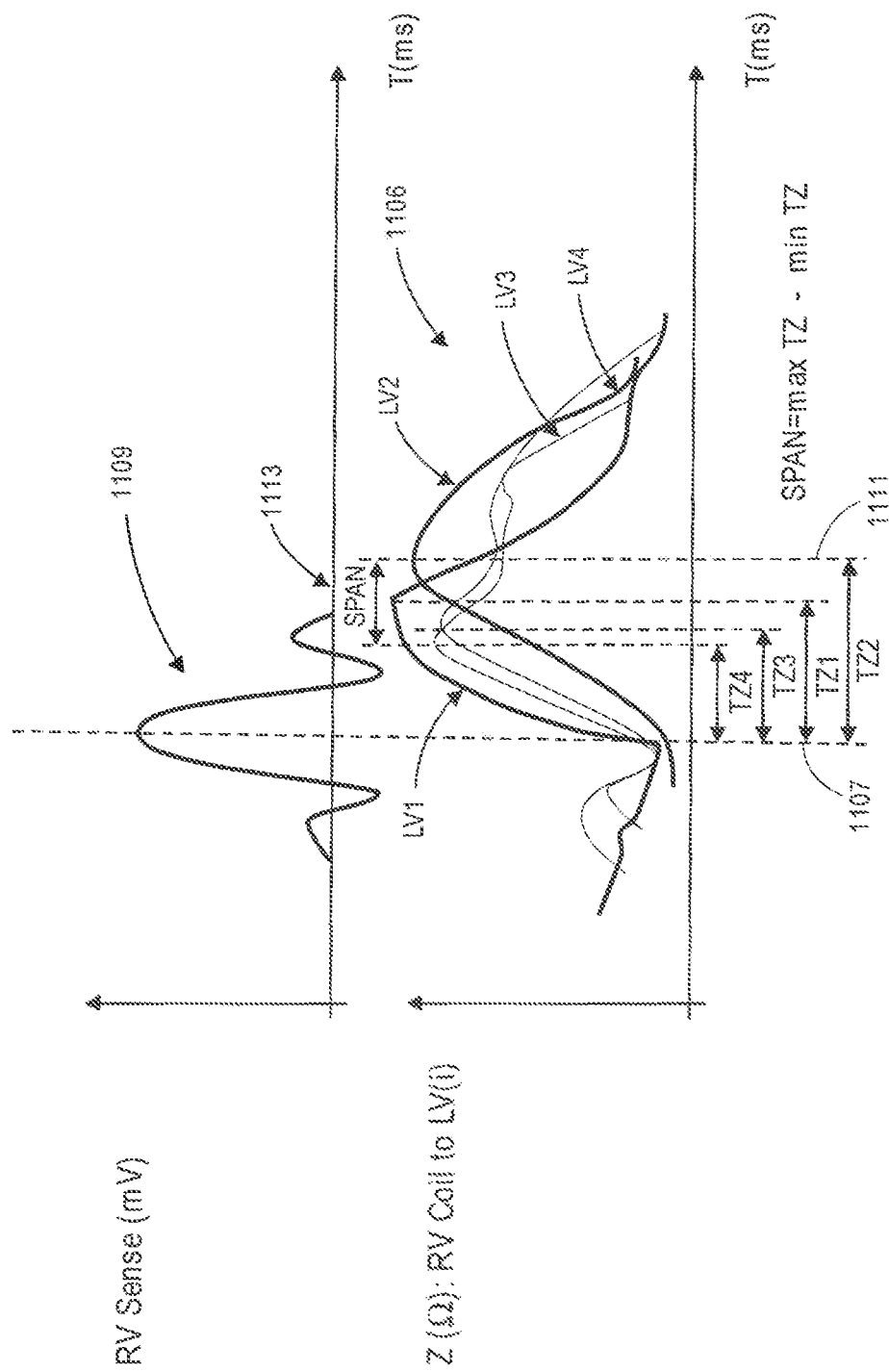
FIG. 11 provides a graph showing four exemplary cardiogenic Z(t) signal traces (LV1, LV2, LV3 and LV4) derived from RV coil to LV and the timing of the corresponding Zmax points within each of the traces in accordance with embodiments herein.

FIG. 11 provides a graph 1106 showing four exemplary cardiogenic Z(t) signal traces (LV1, LV2, LV3 and LV4) derived from RV coil to LV and the timing of the corresponding Zmax points within each of the traces. In the Figure, time 1107 corresponds to the peak of an RV sense signal 1109. Alternatively, other reference points or landmarks using far field IEGM or ECG instead of RV IEGM can be used. Time intervals between the peak of RV QRS and subsequent Zmax points (such as time 1111) for each of the four vectors are shown and denoted TZ1, TZ2, TZ3 and TZ4, respectively. As can be seen, the various time intervals differ significantly in this test subject, indicating a significant degree of mechanical dyssynchrony. The largest difference or "span" between the TZ values (i.e. the difference between the maximum TZ value and the minimum TZ value) is denoted in the Figure as "SPAN" 1113 and is a measure of the degree of mechanical dyssynchrony. The greater the value for the span, the greater the dyssynchrony. Note also that, although FIG. 11 only illustrates timing to max Z, similar methods apply to timing to max dZ/dt or min Z. For example, the time from the peak of RV QRS to max dZ/dt can be used to assess dyssynchrony. Also, from the same signals of Z, stroke volume (SVZ) can be obtained where SVZ-max Z-min Z.

Returning to FIG. 10, at step 1008, the CRT device determines values representative of mechanical dyssynchrony from a comparison of the relative timings (t, t') of the corresponding reference points (Zmax, Zmin) within the measured signals and/or determines values representative of stroke volume from selected reference values (particularly the difference between max Z and min Z.) Techniques for detecting or estimating both systolic and diastolic mechanical dyssynchrony, as well as stroke volume, are discussed below.

After 1008, the process returns to the methods of FIGS. 8 and/or 9 to adjust the $AV_{LV}$ delay and repeat the measures, and thereafter to identify a select $AV_{LV}$ delay that affords a desired degree of mechanical synchrony and/or a desired stroke volume. Optionally, the system may generate warnings, records diagnostics, selects electrodes, adjusts pacing delay values and/or controls other device functions based on the values representative of mechanical dyssynchrony and/or stroke volume.

External Device

Figure 12:
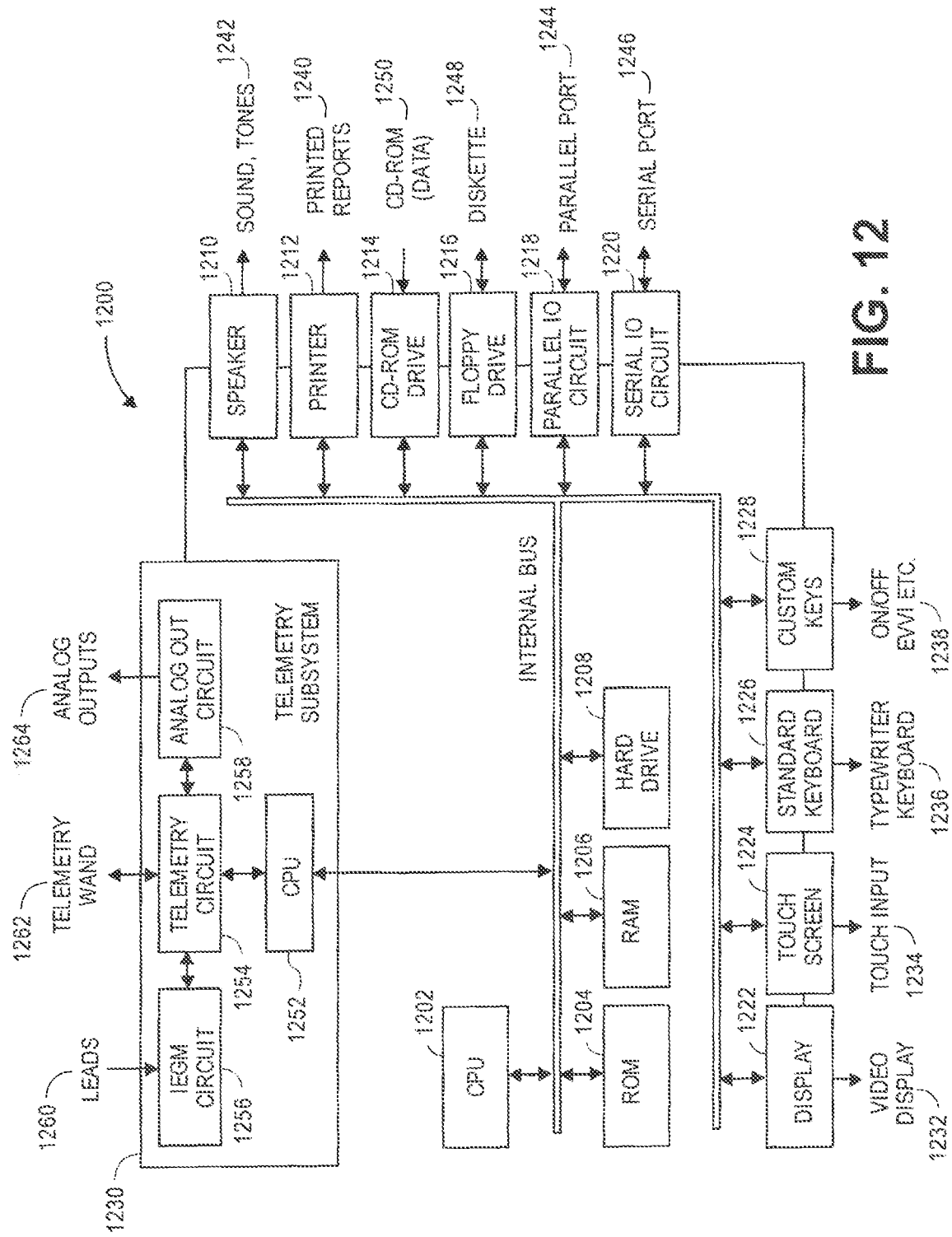
FIG. 12 illustrates a functional block diagram of the external device that is operated in accordance with the processes described herein and to interface with implantable medical devices as described herein.

FIG. 12 illustrates a functional block diagram of the external device 1200 that is operated in accordance with the processes described herein and to interface with implantable medical devices as described herein. The external device 1200 may be a workstation, a portable computer, an IMD programmer, a PDA, a cell phone and the like. The external device 1200 includes an internal bus that connects/interfaces with a Central Processing Unit (CPU) 1202, ROM 1204, RAM 1206, a hard drive 1208, the speaker 1210, a printer 1212, a CD-ROM drive 1214, a floppy drive 1216, a parallel I/O circuit 1218, a serial I/O circuit 1220, the display 1222, a touch screen 1224, a standard keyboard connection 1226, custom keys 1228, and a telemetry subsystem 1230. The internal bus is an address/data bus that transfers information between the various components described herein. The hard drive 1208 may store operational programs as well as data, such as waveform templates and detection thresholds.

The CPU 1202 typically includes a microprocessor, a micro-controller, or equivalent control circuitry, designed specifically to control interfacing with the external device 1200 and with the IMD 100. The CPU 1202 performs the COI measurement process discussed above. The CPU 1202 may include RAM or ROM memory, logic and timing circuitry, state machine circuitry, and I/O circuitry to interface with the IMD 100. The CPU 1202 may implement some or all of the operations of the LUV therapy control circuitry 233 (FIG. 2) and/or the $AV_{LV}$ feedback control circuitry 235 (FIG. 2). The CPU 1202 may implement some or all of the operations of the methods described herein, such as in connection with FIGS. 3-11.

The display 1222 (e.g., may be connected to the video display 1232). The touch screen 1224 may display graphic information relating to the IMD 100. The display 1222 displays various information related to the processes described herein. The touch screen 1224 accepts a user's touch input 1234 when selections are made. The keyboard 1226 (e.g., a typewriter keyboard 1236) allows the user to enter data to the displayed fields, as well as interface with the telemetry subsystem 1230. Furthermore, custom keys 1228 turn on/off 1238 (e.g., EVVI) the external device 1200. The printer 1212 prints copies of reports 1240 for a physician to review or to be placed in a patient file, and speaker 1210 provides an audible warning (e.g., sounds and tones 1242) to the user. The parallel I/O circuit 1218 interfaces with a parallel port 1244. The serial I/O circuit 1220 interfaces with a serial port 1246. The floppy drive 1216 accepts diskettes 1248. Optionally, the floppy drive 1216 may include a USB port or other interface capable of communicating with a USB device such as a memory stick. The CD-ROM drive 1214 accepts CD ROMs 1250.

The telemetry subsystem 1230 includes a central processing unit (CPU) 1252 in electrical communication with a telemetry circuit 1254, which communicates with both an IEGM circuit 1256 and an analog out circuit 1258. The circuit 1256 may be connected to leads 1260. The circuit 1256 is also connected to the implantable leads to receive and process IEGM cardiac signals as discussed above. Optionally, the IEGM cardiac signals sensed by the leads may be collected by the IMD 100 and then transmitted, to the external device 1200, wirelessly to the telemetry subsystem 1230 input.

The telemetry circuit 1254 is connected to a telemetry wand 1262. The analog out circuit 1258 includes communication circuits to communicate with analog outputs 1264. The external device 1200 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 1200 to the IMD 100.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for controlling a left univentricular (LUV) pacing therapy using an implantable medical device (IMD), the method comprising:
   providing electrodes configured to be located proximate to an atrial (A) site, left ventricular (LV) site and right ventricular (RV) site of the heart;
   utilizing one or more processors to perform:
      determining a conduction different $\Delta$ based on i) an atrial-ventricular conduction delay ($AR_{RV}$) between the A site and the RV site, and ii) an atrial-ventricular conduction delay ($AR_{LV}$) between the A site and the LV site;
      determining a correction term $\varepsilon$ based on an intrinsic inter-ventricular conduction delay (IVCD) between the LV and RV;
      setting an interventricular pacing (VV) delay based on the conduction difference $\Delta$, a pacing latency PL and the correction term $\varepsilon$;
      setting an LV atrial-ventricular pacing ($AV_{LV}$) based on the VV delay; and
      managing the LUV pacing therapy based on the $AV_{LV}$ delay, wherein the LUV pacing therapy lacks pacing in the RV.

2. The method of claim 1, wherein the VV delay is set based on the following: VV=FCTR($\Delta*W_1+\varepsilon*W_2+PL*W_3$), where FCTR is any desired non-zero number, and $W_1$-$W_3$ represent weighting factors.

3. The method of claim 2, further comprising:
   determining the atrial-ventricular conduction delay ($AR_{RV}$) between the A site and the RV site; and
   setting the $AV_{LV}$ delay based on a difference between the $AR_{RV}$ and the VV delay.

4. The method of claim 1, further comprising measuring the pacing latency PL by measuring a latency interval between a paced event, delivered at the LV site, and an evoked response, sensed at the LV site.

5. The method of claim 1, further comprising comparing the pacing latency with a threshold and adjusting the VV delay based on the comparison.

6. The method of claim 1, wherein VV delay is set based on the conduction difference $\Delta$ and the correction term $\varepsilon$, and not the pacing latency PL when the pacing latency PL exceeds a threshold.

7. The method of claim 1, further comprising confirming the LUV pacing therapy using at least one of QRS related feedback, mechanical di-synchrony related feedback or stroke volume surrogate related feedback.

8. The method of claim 7, further comprising analyzing a paced QRS width in connection with multiple $AV_{LV}$ delays, and selecting an $AV_{LV}$ delay corresponding to the paced QRS width having a criteria of interest.

9. The method of claim 7, further comprising analyzing a contractility time delay in connection with multiple $AV_{LV}$ delays, and selecting an $AV_{LV}$ delay corresponding to the contractility time delay having a criteria of interest.

10. The method of claim 7, further comprising analyzing a stroke volume impedance in connection with multiple $AV_{LV}$ delays, and selecting an $AV_{LV}$ delay corresponding to the stroke volume impedance having a criteria of interest.

11. A system for controlling a left univentricular (LUV) pacing therapy using an implantable medical device (IMD), the system comprising:
    electrodes configured to be located proximate to an atrial (A) site, left ventricular (LV) site and right ventricular (RV) site of the heart;
    memory to store program instructions;
    one or more processors configured to implement the program instructions to perform:
       determining a conduction different $\Delta$ based on i) an atrial-ventricular conduction delay ($AR_{RV}$) between the A site and the RV site, and ii) an atrial-ventricular conduction delay ($AR_{LV}$) between the A site and the LV site;
       determining a correction term $\varepsilon$ based on intrinsic inter-ventricular conduction delay (IVCD) between the LV and RV;
       setting an interventricular pacing (VV) based on the conduction difference $\Delta$, a pacing latency PL and the correction term $\varepsilon$;
       setting an LV atrial-ventricular pacing ($AV_{LV}$) based on the VV delay; and
       managing the LUV pacing therapy based on the $AV_{LV}$ delay, wherein the LUV pacing therapy lacks pacing in the RV.

12. The system of claim 11, wherein the memory is configured to store the VV delay that is set based on the following: VV=FCTR($\Delta*W_1+\varepsilon*W_2+PL*W_3$), where FCTR is any desired non-zero number, and $W_1$-$W_3$ represent weighting factors.

13. The system of claim 12, wherein the one or more processors are further configured to:
    determine the atrial-ventricular conduction delay ($AR_{RV}$) between the A site and the RV site; and
    set the $AV_{LV}$ delay based on a difference between the $AR_{RV}$ and the VV delay.

14. The system of claim 11, wherein the one or more processors are further configured to measure the pacing latency PL by measuring a latency interval between a paced event, delivered at the LV site, and an evoked response, sensed at the LV site.

15. The system of claim 11, wherein the one or more processors are further configured to compare the pacing latency with a threshold and adjusting the VV delay based on the comparison.

16. The system of claim 11, wherein the one or more processors are further configured to set the VV delay based on the conduction difference $\Delta$ and the correction term $\varepsilon$, and not the pacing latency PL when the pacing latency PL exceeds a threshold.

17. The system of claim 11, wherein the one or more processors are further configured to confirm the LUV pacing therapy using at least one of QRS related feedback, mechanical di-synchrony related feedback or stroke volume surrogate related feedback.

18. The system of claim 17, wherein the one or more processors are further configured to analyze a paced QRS width in connection with multiple $AV_{LV}$ delays, and select an $AV_{LV}$ delay corresponding to the paced QRS width having a criteria of interest.

19. The system of claim 17, wherein the one or more processors are further configured to analyze a contractility time delay in connection with multiple $AV_{LV}$ delays, and select an $AV_{LV}$ delay corresponding to the contractility time delay having a criteria of interest.

20. The system of claim 17, wherein the one or more processors are further configured to analyze a stroke volume impedance in connection with multiple $AV_{LV}$ delays, and select an $AV_{LV}$ delay corresponding to the stroke volume impedance having a criteria of interest.

* * * * *